United States Patent
Moehring et al.

(10) Patent No.: US 11,741,856 B2
(45) Date of Patent: Aug. 29, 2023

(54) SYSTEMS AND METHODS FOR SIMULATING A TYMPANIC MEMBRANE

(71) Applicant: OtoNexus Medical Technologies, Inc., Seattle, WA (US)

(72) Inventors: Mark A. Moehring, Seattle, WA (US); George Gates, Seattle, WA (US); Charlie Corredor, Seattle, WA (US); Chad J. MacDonald, Seattle, WA (US)

(73) Assignee: OtoNexus Medical Technologies, Inc., Bellevue, WA (US)

( * ) Notice: Subject to any disclaimer, the term of this patent is extended or adjusted under 35 U.S.C. 154(b) by 399 days.

(21) Appl. No.: 16/861,463

(22) Filed: Apr. 29, 2020

(65) Prior Publication Data

US 2021/0020072 A1 Jan. 21, 2021

Related U.S. Application Data

(60) Provisional application No. 62/840,829, filed on Apr. 30, 2019.

(51) Int. Cl.
*G09B 23/32* (2006.01)
*A61B 1/00* (2006.01)
(Continued)

(52) U.S. Cl.
CPC .......... *G09B 23/32* (2013.01); *A61B 1/00057* (2013.01); *A61B 1/227* (2013.01); *A61B 8/12* (2013.01); *A61B 8/58* (2013.01)

(58) Field of Classification Search
CPC ...... G09B 23/28; G09B 23/30; G09B 23/306; G09B 23/32; G09B 23/34
See application file for complete search history.

(56) References Cited

U.S. PATENT DOCUMENTS 2,778,125 A 1/1957 Irvin et al.
5,997,307 A * 12/1999 LeJeune, Jr. ......... G09B 23/285
434/270
(Continued)

FOREIGN PATENT DOCUMENTS

CN 203943646 U 11/2014
DE 8712771 U1 11/1987
(Continued)

OTHER PUBLICATIONS

Adam, Rouilly. "AR402/AR402-B Digital Ear Examination Trainer"; Instruction Manual;Publication [online]. 2018 [retrieved Jul. 13, 2020]. Retrieved from the Internet: URL:https://www.enasco.com/medias/Healthcare-Manual-SB52823-SB52824-.pdfcontext=bWFzdGVyIGltYWdlc3w0MTk5NDA0fGFwcGxpY2F0aW9uL3BlanpbWFnZXMvaDVXL2hhMy85NjU3Nzc0Tk4Njg2LnBI(ZnxmMzZmODU5NGQ3MzgzMDJjMGY2MDk40Dc5MGQ5MWExMmM1OTZiZDESOGUzMjZ1ZWQ2YmMwMzVmN2VmOWMxZmQ3: entire document.
(Continued)

*Primary Examiner* — Robert J Utama
*Assistant Examiner* — Correll T French
(74) *Attorney, Agent, or Firm* — Wilson Sonsini Goodrich & Rosati

(57) ABSTRACT

Disclosed herein is a device for modeling properties of an ear. The device includes an artificial tympanic membrane and a housing coupled to the artificial tympanic membrane. The housing defines an interior portion coupled to an interior surface of the artificial tympanic membrane. The interior portion has an adjustable volume or an adjustable type of fluid and an adjustable gas pressure. Adjustment of the volume or type of fluid and the gas pressure changes a membrane movement to produce selected movement properties according to a mobility scale.

19 Claims, 19 Drawing Sheets

(51) Int. Cl.
*A61B 1/227* (2006.01)
*A61B 8/12* (2006.01)
*A61B 8/00* (2006.01)

(56) References Cited

U.S. PATENT DOCUMENTS

| | | | |
|---|---|---|---|
| 6,241,767 | B1 | 6/2001 | Stennert et al. |
| 7,771,356 | B2 | 8/2010 | Voie et al. |
| 7,850,455 | B2 | 12/2010 | Cottler et al. |
| 7,859,455 | B2 | 12/2010 | Gutt et al. |
| 10,043,415 | B2 | 8/2018 | Forte et al. |
| 10,097,923 | B2 | 10/2018 | Ikeda |
| 10,568,515 | B2 | 2/2020 | Moehring et al. |
| 2006/0278245 | A1* | 12/2006 | Gan .................. A61B 5/12 128/897 |
| 2008/0050710 | A1* | 2/2008 | Cottler .............. G09B 23/34 434/270 |
| 2011/0104651 | A1* | 5/2011 | Sweeney ............ G09B 23/12 434/268 |
| 2011/0303227 | A1 | 12/2011 | Pick et al. |
| 2015/0187229 | A1* | 7/2015 | Wachli ............. G09B 23/285 434/272 |
| 2016/0367404 | A1 | 12/2016 | Shomo |
| 2017/0014053 | A1 | 1/2017 | Moehring et al. |
| 2017/0360302 | A1 | 12/2017 | Chesavage et al. |
| 2018/0310917 | A1 | 11/2018 | Moehring et al. |
| 2019/0142258 | A1 | 5/2019 | Shelton et al. |
| 2019/0200873 | A1 | 7/2019 | Chesavage et al. |
| 2019/0365292 | A1 | 12/2019 | Moehring et al. |
| 2020/0107813 | A1 | 4/2020 | Moehring et al. |

FOREIGN PATENT DOCUMENTS

| | | | |
|---|---|---|---|
| TW | 201426680 | A | 7/2014 |
| TW | 201447681 | A | 12/2014 |
| WO | WO-2020223385 | A1 | 11/2020 |
| WO | WO-2022010804 | A1 | 1/2022 |

OTHER PUBLICATIONS

Cavanaugh, Robert M. "Pneumatic otoscopy in healthy full-term infants." Pediatrics 79.4 (1987): 520-523.

GT Stimulators; Diagnostic and Procedural Ear Trainer with Pneumatic Otoscopy Kit, Available at http://www.GTsimulators.com.

Jones, W. et al., "How helpful is pneumatic otoscopy in improving diagnostic accuracy?." Pediatrics 112.3 (2003): 510-513.

Kaleida, P., et al., "Assessment of otoscopists' accuracy regarding middle-ear effusion: otoscopic validation." American Journal of Diseases of Children 146.4 (1992): 433-435.

Morris, et al., Development and Validation of a Novel Ear Simulator to Teach Pneumatic Otoscopy, Simulation in Healthcare7(1): 22-26, 2012.

PCT/US20/30524 Search Report & Written Opinion dated Jul. 30, 2020.

Schwartz, et al., Acute otitis media: Diagnosis and drug therapy. Drugs 19.2 (1980): 107-118.

Shelton, et al.,Quantitative Pneumatic Otoscopy Using a Light-Based Ranging Technique, Journal of the Association for Research in Otolaryngology 18(4): 555-568, 2017.

EP20799128.2 Extended European Search Report dated Nov. 28, 2022.

PCT/US2021/040370 International Search Report and Written Opinion dated Dec. 10, 2021.

\* cited by examiner

SYSTEMS AND METHODS FOR SIMULATING A TYMPANIC MEMBRANE

CROSS-REFERENCE

This application claims the benefit of U.S. Provisional Patent Application No. 62/840,829 filed Apr. 30, 2019, which is incorporated herein by reference in its entirety.

STATEMENT AS TO FEDERALLY SPONSORED RESEARCH

This invention was made with the support of the United States government through Small Business Innovation Research (SBIR) program, grant number 1853244 (Phase II Award), by the National Science Foundation.

BACKGROUND

Otitis media (OM) is a group of inflammatory diseases of the inner ear and the cause of the most prevalent childhood healthcare issue, commonly known as an "ear infection". OM is defined by the presence of a liquid effusion in the middle ear and has the following main types: acute otitis media (AOM), otitis media with effusion (OME), Chronic otitis media (COM), and Chronic suppurative otitis media (CSOM). Rapid onset of infections that usually present with ear pain are characteristic of AOM middle ear effusions (MEE), while OME is not typically associated with symptoms because the MEE fluids are non-infectious.

The accuracy of OM diagnosis depends on the equipment and the skills of the physician. The average rate of misdiagnosis may be in the range of 30%-50%. For example, OME may be misdiagnosed as AOM, and a retracted tympanic membrane without associated middle ear effusion may be misdiagnosed as OME. Given the rate of misdiagnosis, improved devices, systems, and methods for diagnosing OM are desired. As new equipment is developed, it may not be feasible or may not be safe or both to test directly on a human subject.

Accordingly, improved devices, systems, and methods for simulating a tympanic membrane, for example, a diseased tympanic membrane, a disordered tympanic membrane, or a healthy tympanic membrane, are desired.

References which may be relevant to the disclosure herein may include U.S. Pat. Nos. 5,997,307, 7,771,356, 7,859,455, 10,043,415, and 10,097,923; U.S. Patent Publication No. 2019/0142258; Taiwan Application No. 1447681; and Non-Patent Publications Shelton, et al., Quantitative Pneumatic Otoscopy Using a Light-Based Ranging Technique, Journal of the Association for Research in Otolaryngology 18(4): 555-568, 2017; Morris, et al., Development and Validation of a Novel Ear Simulator to Teach Pneumatic Otoscopy, 7(1): 22-26, 2012; and Diagnostic and Procedural Ear Trainer w/Pneumatic Otoscopy Kit, www.GTsimulators.com.

SUMMARY

The present disclosure relates to systems and methods for simulating a tympanic membrane. The simulated membrane may approximate the mobility of a tympanic membrane during various biological states of an ear, such as a disease state or a healthy state. Embodiments of the disclosure may aid in the development of tools for diagnosing ear disorders, such as for example otitis media.

In an aspect, a device for modeling properties of an ear, including a tympanic membrane is provided. The device may comprise: an artificial tympanic membrane having an ultrasound reflectivity mimicking an ultrasound reflectivity of a biological tympanic membrane; and a housing coupled to the artificial tympanic membrane and further defining an interior portion coupled to an interior surface of the artificial tympanic membrane, the interior portion having an adjustable volume of fluid or an adjustable type of fluid, and the interior portion having an adjustable gas pressure.

In some embodiments, adjustment of one or more of the volume of fluid, the type of fluid, or the gas pressure changes a membrane deflection or a membrane movement to controllably mimic a disease state of an ear. In some embodiments, adjustment of the type of fluid comprises varying a viscosity of fluid. In some embodiments, the disease state of the ear is a bacterial or a viral ear infection.

In some embodiments, the artificial tympanic membrane has a shape which exhibits an optical reflection from the artificial tympanic membrane surface to enable location of the artificial tympanic membrane and alignment of an otoscope. In some embodiments, the optical reflection is exhibited on an anterior inferior quadrant of the artificial tympanic membrane. In some embodiments, the artificial tympanic membrane has one or more visual cues, wherein the visual cues comprise exhibiting at least partially a shape of an umbo or a malleus.

In some embodiments, the artificial tympanic membrane is one or more of distensible or retractable and is further configured to move in response to an applied pneumatic pressure change. In some embodiments, the movement of the artificial tympanic membrane is adjustable according to a set of ordinal values. In some embodiments, the movement of the artificial tympanic membrane is adjustable according to a continuous scale. In some embodiments, adjustment of one or more of the volume of fluid, the type of fluid, or the gas pressure changes a rate of the membrane movement to controllably mimic a disease state of an ear. In some embodiments, the housing further defines an exterior portion, wherein the external portion comprises an artificial ear canal having an approximate geometry of a human pediatric subject or a human adult subject. In some embodiments, the interior portion comprises a mock ossicular chain coupled to the tympanic membrane. In some embodiments, the mock ossicular has a controllable tension. In some embodiments, a shape and a durometer of the artificial tympanic membrane is configured to mimic a presence of an ossicular chain.

In some embodiments, the interior portion comprises a fluid injector or an opening for a fluid injector. In some embodiments, the interior portion comprises an internal air valve and an internal air pump or an opening for an internal air valve and an internal air pump. In some embodiments, the interior portion comprises an internal pressure gauge or an opening for an internal pressure gauge. In some embodiments, the housing further defines an exterior portion coupled to an exterior surface of the artificial tympanic membrane. In some embodiments, the exterior portion comprises an external pressure gauge or an opening for an external pressure gauge. In some embodiments, the exterior portion comprises an external air pump or an opening for an external ear pump.

In some embodiments, the device of any aspect or embodiment, further comprises a processor configured to control the operation of one or more of: the fluid injector, the internal air valve, the internal air pump, the internal pressure gauge, the external pressure gauge, the external air pump, or a display visible to a user. In some embodiments, the processor is configured to receive pressure data from one or more of the internal pressure gauge or the external pressure gauge. In some embodiments, the pressure data is used to adjust one or more of: the volume of fluid proximate the interior surface; the pressure of gas proximate the interior surface; and the pressure of gas proximate the exterior surface.

In another aspect, a method of testing an otoscope using a model ear, including an artificial tympanic membrane, is provided. The method may comprise: providing an artificial tympanic membrane having an ultrasound reflectivity mimicking an ultrasound reflectivity of a biological tympanic membrane; adjusting a volume of or a type of fluid proximate an interior surface of the artificial tympanic membrane; adjusting a pressure of gas proximate an interior surface of the artificial tympanic membrane.

In some embodiments, the adjusting of one or more of the volume of fluid, the type of fluid, or the pressure of gas changes a membrane deflection or a membrane movement to controllably mimic a disease state of an ear. In some embodiments, adjusting the type of fluid comprises varying a viscosity of fluid. In some embodiments, the disease state of the ear is a bacterial or a viral ear infection.

In some embodiments, the method further comprises aligning an otoscope to locate the artificial tympanic membrane based on an optical reflection from the artificial tympanic membrane surface. In some embodiments, the optical reflection is exhibited on an anterior inferior quadrant of the artificial tympanic membrane. In some embodiments, the artificial tympanic membrane has one or more visual cues, wherein the visual cues comprise exhibiting at least partially a shape of an umbo or a malleus.

In some embodiments, the method further comprises adjusting a movement of the artificial tympanic membrane according to a set of ordinal values. In some embodiments, the method further comprises adjusting a movement of the artificial tympanic membrane according to a continuous scale. In some embodiments, the method further comprises directing a speculum of an acoustic otoscope toward the artificial tympanic membrane, wherein the artificial tympanic membrane is at least one of distensible or retractable and is configured to move in response to an applied pneumatic pressure change. In some embodiments, the adjusting of one or more of the volume of fluid, the type of fluid, or the gas pressure changes a rate of the membrane movement to controllably mimic a disease state of an ear.

In some embodiments, the method further comprises providing an artificial ear canal having an approximate geometry of a human pediatric subject or a human adult subject. In some embodiments, the method further comprises adjusting a tension in a mock ossicular chain coupled to the artificial tympanic membrane. In some embodiments, a shape and a durometer of the artificial tympanic membrane is configured to mimic a presence of an ossicular chain.

In some embodiments, the method further comprises injecting a fluid proximate the interior surface using a fluid injector. In some embodiments, the adjusting the pressure of gas proximate the interior surface comprises opening or closing an internal air valve and activating an internal air pump. In some embodiments, the method further comprises measuring the pressure of gas proximate the interior surface using an internal pressure gauge. In some embodiments, the method further comprises measuring the pressure of gas proximate an exterior surface of the artificial tympanic membrane using an external pressure gauge. In some embodiments, the method further comprises adjusting the pressure of gas proximate an exterior surface of the artificial tympanic membrane using an external air pump.

In some embodiments, the method further comprises using a processor to control the operation of one or more of the fluid injector, the internal air valve, the internal air pump, the internal pressure gauge, the external pressure gauge, the external air pump, or a display visible to a user. In some embodiments, the method further comprises receiving pressure data from one or more of the internal pressure gauge or the external pressure gauge at a processor. In some embodiments, the method further comprises using the pressure data to adjust one or more of: the volume of fluid proximate the interior surface; the pressure of gas proximate the interior surface; and the pressure of gas proximate the exterior surface.

In another aspect, a device for modeling properties of an ear, including a tympanic membrane, is provided. The device may comprise: an artificial tympanic membrane; a housing coupled to the artificial tympanic membrane and further defining an interior portion coupled to an interior surface of the artificial tympanic membrane, the interior portion having an adjustable volume of fluid and an adjustable gas pressure; wherein adjustment of the volume of fluid and the gas pressure changes a membrane movement to produce selected movement properties according to a mobility scale.

In some embodiments, the mobility scale is a set of ordinal values. In some embodiments, the mobility scale is a continuous scale. In some embodiments, the artificial tympanic membrane is distensible or retractable and is configured to move in response to an applied pneumatic pressure change. In some embodiments, the adjustment of one or more of the volume of fluid, the type of fluid, or the pressure of gas changes a membrane deflection or a membrane movement to controllably mimic the disease state of the ear. In some embodiments, the adjustment of the type of fluid comprises varying a viscosity of fluid. In some embodiments, the disease state of the ear is a bacterial or a viral ear infection.

In some embodiments, the artificial tympanic membrane has a shape which exhibits an optical reflection from the artificial tympanic membrane surface to enable location of the artificial tympanic membrane and alignment of an otoscope. In some embodiments, the optical reflection is exhibited on the anterior inferior quadrant of the artificial tympanic membrane. In some embodiments, the artificial tympanic membrane has one or more visual cues, wherein the visual cues comprise exhibiting at least partially a shape of an umbo or a malleus. In some embodiments, the housing further defines an exterior portion, wherein the external portion comprises an artificial ear canal having an approximate geometry of a human pediatric subject or a human adult subject. In some embodiments, the interior portion comprises a mock ossicular chain coupled to the tympanic membrane. In some embodiments, the mock ossicular has a controllable tension. In some embodiments, a shape and a durometer of the artificial tympanic membrane is configured to mimic a presence of an ossicular chain.

In some embodiments, the interior portion comprises a fluid injector or an opening for a fluid injector. In some embodiments, the interior portion comprises an internal air valve and an internal air pump or an opening for an internal air valve and an internal air pump. In some embodiments, the interior portion comprises an internal pressure gauge or an opening for an internal pressure gauge. In some embodiments, the housing further defines an exterior portion coupled to an exterior surface of the artificial tympanic membrane. In some embodiments, the exterior portion comprises an external pressure gauge or an opening for an external pressure gauge. In some embodiments, the exterior portion comprises an external air pump or an opening for an external air pump.

In some embodiments, the device further comprises a processor configured to control the operation of one or more of: the fluid injector, the internal air valve, the internal air pump, the internal pressure gauge, the external pressure gauge, the external air pump, or a display visible to a user. In some embodiments, the processor is configured to receive pressure data from one or more of the internal pressure gauge or the external pressure gauge. In some embodiments, the pressure data is used to adjust one or more of: the volume of fluid proximate the interior surface; the pressure of gas proximate the interior surface; and the pressure of gas proximate the exterior surface In another aspect, a method of testing an otoscope using a model ear, including an artificial tympanic membrane, is provided. The method may comprise: providing an artificial tympanic membrane; adjusting a volume or a type of fluid proximate an interior surface of the artificial tympanic membrane; adjusting a pressure of gas proximate an interior surface of the artificial tympanic membrane; wherein the adjusting of the volume or the type of fluid and the adjusting of the pressure of gas changes a membrane movement to produce selected movement properties according to a mobility scale.

In some embodiments, the adjusting one or more of the volume of fluid, the type of fluid, or the pressure of gas changes a membrane deflection or a membrane movement to controllably mimic the disease state of the ear. In some embodiments, the disease state of the ear is a bacterial or a viral ear infection. In some embodiments, the disease state of the ear is a bacterial or a viral ear infection. In some embodiments, the mobility scale comprises a set of ordinal values. In some embodiments, the mobility scale comprises a continuous scale.

In some embodiments, wherein the method further comprises aligning an otoscope to locate the artificial tympanic membrane based on an optical reflection from the artificial tympanic membrane surface. In some embodiments, the optical reflection is exhibited on an anterior inferior quadrant of the artificial tympanic membrane. In some embodiments, the artificial tympanic membrane has one or more visual cues, wherein the visual cues comprise exhibiting at least partially a shape of an umbo or a malleus.

In some embodiments, the method further comprises directing a speculum of an acoustic otoscope toward the artificial tympanic membrane, wherein the artificial tympanic membrane is at least one of distensible or retractable and is configured to move in response to an applied pneumatic pressure change. In some embodiments, the adjusting of one or more of the volume of fluid, the type of fluid, or the gas pressure changes a rate of the membrane movement to controllably mimic a disease state of an ear. In some embodiments, the method further comprises providing an artificial ear canal having an approximate geometry of a human pediatric subject or a human adult subject. In some embodiments, the interior portion comprises a mock ossicular chain coupled to the tympanic membrane. In some embodiments, the method further comprises adjusting a tension in a mock ossicular chain coupled to the artificial tympanic membrane. In some embodiments, a shape and a durometer of the artificial tympanic membrane is configured to mimic a presence of an ossicular chain.

In some embodiments, the method further comprises injecting a fluid proximate the interior surface using a fluid injector. In some embodiments, the adjusting the pressure of gas proximate the interior surface comprises opening or closing an internal air valve and activating an internal air pump. In some embodiments, the method further comprises measuring the pressure of gas proximate the interior surface using an internal pressure gauge. In some embodiments, the method further comprises measuring the pressure of gas proximate an exterior surface of the artificial tympanic membrane using an external pressure gauge. In some embodiments, the method further comprises adjusting the pressure of gas proximate an exterior surface of the artificial tympanic membrane using an external air pump.

In some embodiments, the method further comprises using a processor to control the operation of one or more of the fluid injector, the internal air valve, the internal air pump, the internal pressure gauge, the external pressure gauge, the external air pump, or a display visible to a user. In some embodiments, the method further comprises receiving pressure data from one or more of the internal pressure gauge or the external pressure gauge. In some embodiments, the method further comprises using the pressure data to adjust one or more of: the volume of fluid proximate the interior surface; the pressure of gas proximate the interior surface; and the pressure of gas proximate the exterior surface.

In another aspect, a device for modeling properties of an ear, including a tympanic membrane, is provided. The device may comprise: an artificial tympanic membrane; and a housing coupled to the artificial tympanic membrane and further defining an interior portion coupled to an interior surface of the artificial tympanic membrane, the interior portion having an adjustable volume or type of fluid and an adjustable gas pressure; wherein adjustment of two or more of the volume or the type of fluid and the gas pressure changes a membrane deflection or a membrane movement to controllably mimic a disease state of an ear.

In another aspect, a method of testing an otoscope using a model ear, including an artificial tympanic membrane, is provided. The method may comprise: providing an artificial tympanic membrane; adjusting a volume of or a type of fluid proximate an interior surface of the artificial tympanic membrane; adjusting a pressure of gas proximate an interior surface of the artificial tympanic membrane, wherein the adjusting one or more of the volume of fluid, the type of fluid, or the pressure of gas changes a membrane deflection or a membrane movement to controllably mimic a disease state of an ear.

In another aspect, a system for simulating a tympanic membrane is provided. The system may comprise: a main chamber; a membrane, wherein the membrane is supported within the main chamber, wherein the membrane separates an interior of the main chamber from an exterior of the main chamber, and wherein the membrane is secured by a membrane clamp; and an elastomeric spring, wherein the elastomeric spring couple to the membrane and wherein the elastomeric spring is secured by a spring clamp; wherein at least one of a mass of the membrane, a damping of the elastomeric spring, a spring rate, a pressure in the interior of the main chamber, and an amount of fluid in the interior of the main chamber are selectively controlled to approximate conditions within an ear.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

DETAILED DESCRIPTION

Figure 1A:
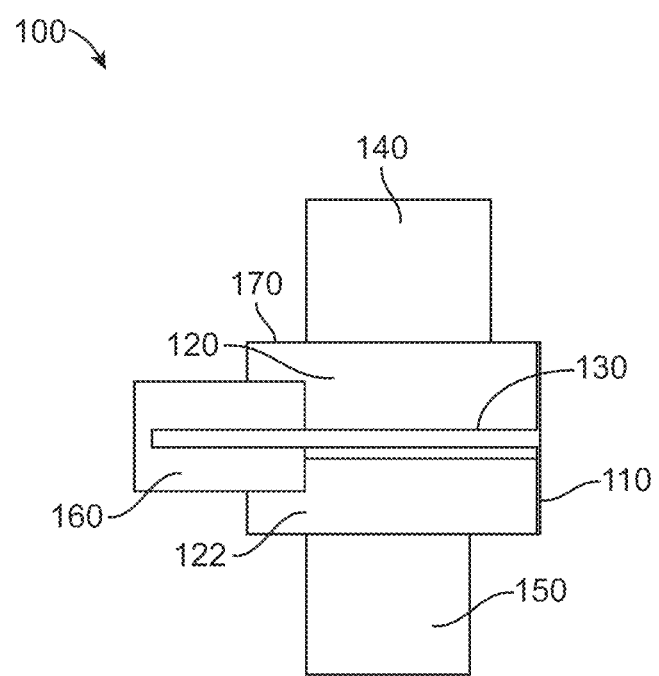
FIG. 1A illustrates a schematic of a device for modeling properties of an ear comprising an interior portion with a mock ossicular chain, in accordance with some embodiments.

The present disclosure relates to devices, methods, and systems for modeling properties of an ear using an artificial model of an ear (also referred to herein as a "phantom"). Devices, methods, and systems herein may be used in connection with pneumatic or other otoscopes. A pneumatic otoscope may apply a pressure challenge to an ear drum and properties of the tympanic membrane may be measured in response to a pneumatic challenge. Improved devices, methods, and systems for simulating a tympanic membrane may allow for testing of otoscope devices (e.g. acoustic otoscope devices) without need of a subject, before use with a subject, etc. Devices, methods, and systems disclosed herein may allow for more rapid prototyping, for safer testing of prototypes, etc. An artificial model of an ear may sufficiently simulate various properties of an ear, such as membrane movement, membrane displacement, optical reflectivity, ultrasound reflectivity, etc. to allow for testing of otoscope devices, for example, acoustic otoscope devices and/or pneumatic otoscope devices. An artificial model of an ear may be adjustable to mimic a particular disease state of an ear. An artificial model of an ear may be adjustable to mimic membrane movement or displacement characteristics of a tympanic membrane. An artificial tympanic membrane may be adjustable according to a mobility scale. Clinical diagnostic tests may employ ordinal scales to categorize membrane characteristics. Accordingly, it may be beneficial to design an artificial tympanic membrane which mimics particular movement characteristic according to a clinical scale.

The device, methods, and systems as disclosed herein may be used in combination with for example devices and methods to characterize a ductile membrane, surface, and sub-surface properties such as those described in commonly owned U.S. Pat. No. 7,771,356 and U.S. Patent Publication Nos. 2019/0365292, 2018/0310917, and 2017/0014053, each of which is incorporated by reference in their entireties. The methods, systems, and media as disclosed herein may be used in combination with for example devices and methods using optical coherence tomography (OCT), as disclosed in commonly assigned U.S. Patent Publication No.

2019/0200873 and U.S. Patent Publication No. 2017/0360302, each of which is incorporated herein by reference in its entirety.

The devices, methods, and systems as disclosed herein may use an ear as an example membrane. In some cases, the device, methods, and systems disclosed herein may be used to simulate a number of biological tissues to provide a variety of diagnostic information. A biological tissue may comprise a patient organ. A speculum may be disposed within a bodily cavity to characterize a patient tissue. A patient organ or bodily cavity may comprise, for example, a muscle, a tendon, a ligament, a mouth, a tongue, a pharynx, an esophagus, a stomach, an intestine, an anus, a liver, a gallbladder, a pancreas, a nose, a larynx, a trachea, lungs, a kidneys, a bladder, a urethra, a uterus, a vagina, an ovary, a testicle, a prostate, a heart, an artery, a vein, a spleen, a gland, a brain, a spinal cord, a nerve, etc, to name a few.

The devices, methods, and systems as disclosed herein may be used to simulate one or more properties of a tympanic membrane. The devices, methods, and systems as disclosed herein may comprise an artificial tympanic membrane. For example, an artificial tympanic membrane membrane may simulate various conditions of an ear, such as acute otitis media (AOM), chronic otitis media, otitis media with effusion and/or chronic suppurative otitis media. A classification that an ear exhibits AOM may include detection of the presence of effusion and characterization of the type of effusion as one of serous, mucoid, purulent, or combinations of these. In AOM, the middle ear effusion (MEE) may be induced by infective agents and may be thin or serous with viral infection and thicker and purulent with bacterial infection. Accordingly, simulating a diseased state or a healthy state of an ear may comprise simulating various properties of a fluid adjacent a tympanic membrane, such as a type of fluid, a viscosity of fluid, etc. Simulating a diseased state or a healthy state of an ear may comprise simulating a pressure within an ear. Simulating a diseased state or a healthy state of an ear may comprise simulating a tension or a shape of tympanic membrane. For example, a membrane may be distended or retracted.

Reference will now be made in detail to various embodiments, examples of which are illustrated in the accompanying drawings. In the following detailed description, numerous specific details are set forth in order to provide a thorough understanding of the present disclosure and the described embodiments. However, the embodiments of the present disclosure are optionally practiced without these specific details. In other instances, well-known methods, procedures, components, and circuits have not been described in detail so as not to unnecessarily obscure aspects of the embodiments. In the drawings, like reference numbers designate like or similar steps or components.

The terminology used herein is for the purpose of describing particular embodiments only and is not intended to be limiting of the claims. As used in the description of the embodiments and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, the terms "comprises", "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "subject" and "patient" are used interchangeably. As used herein, the terms "subject" and "subjects" refers to an animal (e.g., birds, reptiles, and mammals), a mammal including a primate (e.g., a monkey, chimpanzee, and a human) and a non-primate (e.g., a camel, donkey, zebra, cow, pig, horse, cat, dog, rat, and mouse). In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100.

Disclosed herein is a device for modeling properties of an ear. The device may model properties of an ear including properties of a tympanic membrane. In some embodiments, the device comprises an artificial tympanic membrane. The artificial tympanic membrane may have an ultrasound reflectivity which mimics an ultrasound reflectivity of a biological tympanic membrane. The artificial tympanic membrane may have an optical reflectivity which mimics a biological tympanic membrane. The device may comprise a housing coupled to the artificial tympanic membrane. The housing may define an interior portion, which may be coupled to an interior surface of the artificial tympanic membrane. The interior portion may have an adjustable volume of fluid or an adjustable type of fluid. The interior portion may have an adjustable gas pressure.

Disclosed herein is a device for modeling properties of an ear. The device may include a tympanic membrane. The device may comprise an artificial tympanic membrane. The device may comprise a housing coupled to the artificial tympanic membrane. The housing may define an interior portion coupled to an interior surface of the artificial tympanic membrane. The interior portion may have an adjustable volume or type of fluid and an adjustable gas pressure. Adjustment two or more of the volume or the type of fluid and the gas pressure may change a membrane deflection or a membrane movement to controllably mimic a disease state of an ear.

Disclosed herein is a device for modeling properties of an ear. The device may include a tympanic membrane. The device may comprise an artificial tympanic membrane. The device may comprise a housing coupled to the artificial tympanic membrane. The housing may define an interior portion coupled to an interior surface of the artificial tympanic membrane. The interior portion may have an adjustable volume or an adjustable type of fluid and an adjustable gas pressure. Adjustment of the volume or type of fluid and the gas pressure changes a membrane movement to produce selected movement properties according to a mobility scale.

Also disclosed herein are systems comprising a device for modeling properties of an ear including a tympanic membrane. Systems disclosed herein may comprise a device of the present disclosure and one more additional component, for example, a digital processing device, an air subsystem, a liquid subsystem, an electrical subsystem, an artificial external ear, an interrogation device (e.g. an otoscope), and any combination thereof.

Disclosed herein is a system for simulating a tympanic membrane. The system may comprise a main chamber. The system may comprise a membrane. The membrane may be supported within the main chamber. The membrane may separate an interior of the main chamber from an exterior of the main chamber. The membrane may be secured within the main chamber by a clamp. The system may comprise an elastomeric spring. The elastomeric spring may be coupled to the membrane and secured by a spring clamp. In some cases, at least one of a mass of the membrane, a damping of the elastomeric spring, a spring rate, a pressure in the interior of the main chamber, and an amount of fluid in the interior of the main chamber may be selectively controlled to approximate conditions within an ear.

FIG. 1A illustrates a schematic of device 100 for modeling properties of an ear, the device 100 comprising an interior portion with a mock ossicular chain, in accordance with some embodiments. The device may comprise housing 170. Housing 170 may comprise interior portion 120. Housing 170 may comprise an elastic material 130, which may act as a mock ossicular chain. Housing 170 may comprise a fluid injector 150 coupled to the housing. Housing 170 may comprise an air valve or an air pump 140 coupled to the housing. A housing may comprise a main chamber divided by an artificial tympanic membrane and comprising at least an interior and, optionally, an exterior portion.

A housing 170 may comprise an artificial tympanic membrane 110. Membrane 110 may comprise a material with properties which mimic biological tympanic membrane. For example, membrane 110 may mimic a tension and/or a shape of biological tympanic membrane. For example, a membrane 110 may be distended or retracted to mimic a biological tympanic membrane. A membrane may distend or retract to mimic a healthy state or a diseased state of an ear. A membrane may move in response to an applied pneumatic challenge. A rate of membrane movement in response to an applied pneumatic challenge may mimic a disease state or a healthy state of an ear. Membrane 110 may have a shape which displays visual cues which mimic a visual appearance of biological tympanic membrane. For example, a surface of an artificial tympanic membrane may have visual shape of a malleus or an umbo or both. A tympanic membrane may have a reflectivity for ultrasound which mimics a biological ultrasound reflectivity.

The interior portion may comprise a liquid. A liquid volume 122 may be adjustable to simulate an amount of fluid behind a tympanic membrane. In some cases, a type of fluid may be adjustable to simulate properties of a biological fluid. For example, a type of fluid may be changed to raise or lower a viscosity of a fluid behind a membrane. Changing a viscosity of a fluid may alter a motion or a rate of motion of a tympanic membrane. For example, a more viscous fluid may reduce the effective elasticity of a tympanic membrane. In some cases, the interior portion comprises a fluid injector or an opening for a fluid injector. The fluid injector may be used to raise or lower a volume of a liquid. The fluid injector may be used to change a type of liquid.

In some cases, the type of liquid may be water. In some cases, the type of fluid may a solution. In some cases, a type of fluid may be an aqueous solution. A viscosity of an aqueous solution may be changed by controlling an amount of a solute in a solvent. For example, sodium chloride, potassium iodide, sugar, etc. may be added to water to change a viscosity. In some cases, the type of liquid may be honey. In some cases, a type of liquid may be an oil, such as olive oil, linseed oil, castor oil, motor oil, mineral oil, silicone oil, etc. In some cases, a type of liquid may be a suspension of two immiscible liquids. In some cases, a type of fluid may be a suspension of an oil and water. In some cases, a fluid may be a paste, a gel, or another semisolid. In some cases, a fluid may be a viscoelastic polymer. A viscosity of a fluid may be changed with temperature. For example, at room temperature a viscosity of a fluid may be varied between 100 microPascal seconds, e.g. a light fluid, to 5000 Pascal seconds, e.g. honey.

Interior portion 120 may comprise an adjustable air volume. The air volume may be adjusted to simulate a pressure behind a tympanic membrane. A pressure behind a tympanic membrane may adjust a motion or a rate of motion of a tympanic membrane. For example, a higher pressure behind a tympanic membrane may reduce a motion or a rate of motion a tympanic membrane. In some cases, the interior portion comprises an internal air valve. A device 100 may comprise an internal air pump. A device 100 may comprise an opening for an internal air valve. A device 100 may comprise an opening for an internal air pump. In some case, the interior portion comprises an internal pressure gauge or an opening for an internal pressure gauge. Pressure within an interior portion may be regulated by a pump. Pressure with an interior portion may be regulated by raising or lower the pressure with a pump and sealing the interior portion with a valve. A pressure within an interior portion may be monitored with a gauge. A pressure within an interior portion may be continuously monitored or periodically monitored.

In some cases, a type of a gas may be air. A gas may comprise nitrogen, oxygen, helium, hydrogen, carbon dioxide, helium, krypton, argon, etc., and any combination thereof. A gas may comprise an inert gas. A gas may comprise an elemental gas. A pressure of gas may be varied from several millitorr to 100 kilotorr. Biological ear pressures may typically be about 760 Torr.

In some cases, the interior portion 120 may comprise an elastic material 130 coupled to an artificial tympanic membrane. In some cases, the interior portion comprises a mock ossicular chain coupled to the tympanic membrane. In some case, an elastic material coupled to an artificial tympanic membrane is a spring, e.g. an elastomeric spring. In some cases, an elastic material coupled to an artificial tympanic membrane has a controllable tension. A mock ossicular may have a controllable tension. FIG. 1A shows a spring adjustor

160 coupled to elastic material 130. The spring adjustor may control a tension to adjust an elasticity of an artificial tympanic membrane 110.

Figure 1B:
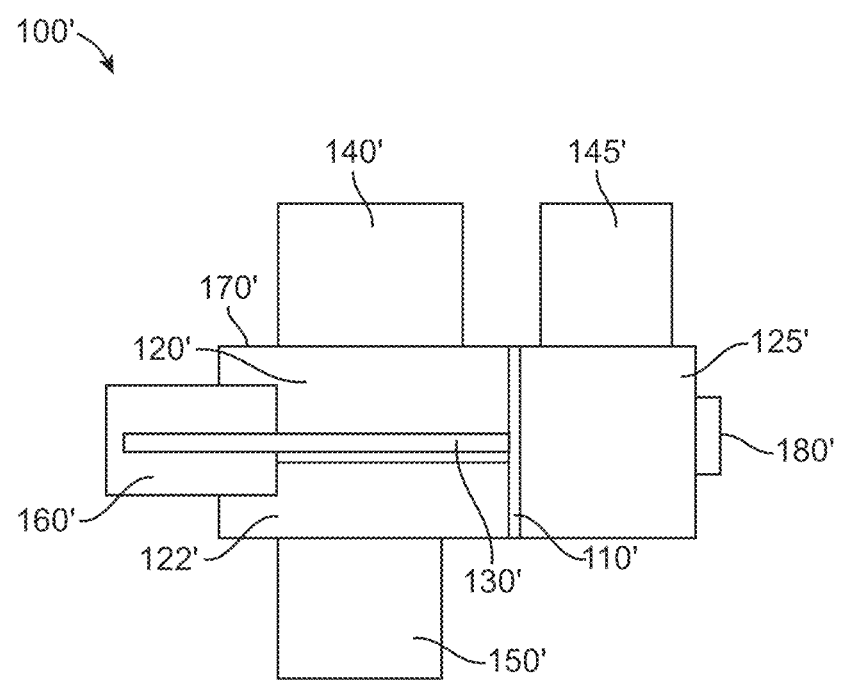
FIG. 1B illustrates a schematic of a device for modeling properties of an ear comprising an interior portion with a mock ossicular chain and an exterior portion with a seal, in accordance with some embodiments.

FIG. 1B illustrates a schematic of device 100' for modeling properties of an ear, the device 100' comprising an interior portion with a mock ossicular chain and an exterior portion with a seal, in accordance with some embodiments. The device may comprise housing 170'. Housing 170' may comprise interior portion 120'. Housing 170' may comprise an elastic material 130', which may act as a mock ossicular chain. Housing 170' may comprise a fluid injector 150' coupled to the housing. Housing 170' may comprise an internal air valve or an internal air pump 140' coupled to the housing. A housing may comprise a main chamber divided by an artificial tympanic membrane and comprising at least an interior and an exterior portion 125'. Housing 170' may comprise an external air valve or an external air pump 145' coupled to the housing. Housing 170' may comprise a seal 180' coupled to the housing.

A housing 170' may comprise an artificial tympanic membrane 110'. Membrane 110' may comprise a material with properties which mimic biological tympanic membrane. For example, membrane 110' may mimic a tension or a shape of biological tympanic membrane. For example, a membrane 110' may be distended or retracted to mimic a biological tympanic membrane. A membrane may distend or retract to mimic a healthy state or a diseased state of an ear. A membrane may move in response to an applied pneumatic challenge. A rate of membrane movement in response to an applied pneumatic challenge may mimic a disease state or a healthy state of an ear. Membrane 110' may have shape which displays visual cues which mimic a visual appearance of biological tympanic membrane. For example, a surface of an artificial tympanic membrane may have visual shape of a malleus or an umbo or both. A tympanic membrane may have a reflectivity for ultrasound which mimics a biological ultrasound reflectivity.

The interior portion may comprise a liquid. A liquid volume 122' may be adjustable to simulate an amount of fluid behind a tympanic membrane. In some cases, a type of fluid may be adjustable to simulate properties of a biological fluid. For example, a type of fluid may be changed to raise or lower a viscosity of a fluid behind a membrane. Changing a viscosity of a fluid may alter a motion or a rate of motion of a tympanic membrane. For example, a more viscous fluid may reduce the effective elasticity of a tympanic membrane. In some cases, the interior portion comprises a fluid injector or an opening for a fluid injector. The fluid injector may be used to raise or lower a volume of a liquid. The fluid injector may be used to change a type of liquid.

In some cases, the type of liquid may be water. In some cases, the type of fluid may a solution. In some cases, a type of fluid may be an aqueous solution. A viscosity of an aqueous solution may be changed by controlling an amount of a solute in a solvent. For example, sodium chloride, potassium iodide, sugar, etc. may be added to water to change a viscosity. In some cases, the type of liquid may be honey. In some cases, a type of liquid may be an oil, such as olive oil, linseed oil, castor oil, motor oil, mineral oil, silicone oil, etc. In some cases, a type of liquid may be a suspension of two immiscible liquids. In some cases, a type of fluid may be a suspension of an oil and water. In some cases, a fluid may be a paste, a gel, or another semisolid. In some cases, a fluid may be a viscoelastic polymer. A viscosity of a fluid may be changed with temperature. For example, at room temperature a viscosity of a fluid may be varied between 100 microPascal seconds, e.g. a light fluid, to 5000 Pascal seconds, e.g., honey.

Interior portion 120' may comprise an adjustable air volume. The air volume may be adjusted to simulate a pressure behind a tympanic membrane. A pressure behind a tympanic membrane may adjust a motion or a rate of motion of a tympanic membrane. For example, a higher pressure behind a tympanic membrane may reduce a motion or a rate of motion of a tympanic membrane. In some cases, the interior portion comprises an internal air valve. A device 100' may comprise an internal air pump. A device 100' may comprise an opening for an internal air valve. A device 100' may comprise an opening for an internal air pump. In some case, the interior portion comprises an internal pressure gauge or an opening for an internal pressure gauge. Pressure within an interior portion may be regulated by a pump. Pressure with an interior portion may be regulated by raising or lower the pressure with a pump and sealing the interior portion with a valve. A pressure within an interior portion may be monitored with a gauge. A pressure within an interior portion may be continuously monitored or periodically monitored.

In some cases, a type of a gas may be air. A gas may comprise nitrogen, oxygen, helium, hydrogen, carbon dioxide, helium, krypton, argon, etc., and any combination thereof. A gas may comprise an inert gas. A gas may comprise an elemental gas. A pressure of gas may be varied from several millitorr to 100 kilotorr. Biological ear pressures may typically be about 760 Torr.

In some cases, the interior portion 120' may comprise an elastic material 130' coupled to an artificial tympanic membrane. In some cases, the interior portion comprises a mock ossicular chain coupled to the tympanic membrane. In some case, an elastic material coupled to an artificial tympanic membrane is a spring, e.g., an elastomeric spring. In some cases, an elastic material coupled to an artificial tympanic membrane has a controllable tension. A mock ossicular may have a controllable tension. FIG. 1B shows a spring adjustor 160' coupled to elastic material 130'. The spring adjustor may control a tension to adjust an elasticity of an artificial tympanic membrane 110'.

A device 100' may comprise an exterior portion 125' coupled to an exterior surface of the artificial tympanic membrane. Exterior portion 125' may comprise an adjustable air volume or pressure. The air volume or pressure may be adjusted to simulate an applied pressure to a tympanic membrane. A pressure applied to a tympanic membrane may be a pneumatic challenge. For example, a pneumatic challenge may induce membrane movement which may be measured by an interrogation device, e.g. an otoscope. In some cases, the external portion comprises an external air valve. A device 100' may comprise an external air pump. A device 100' may comprise an opening for an external air valve. A device 100' may comprise an opening for an external air pump. In some case, the exterior portion comprises an external pressure gauge or an opening for an external pressure gauge. Pressure within an external portion may be regulated by a pump. Pressure with an exterior portion may be regulated by raising or lower the pressure with a pump and sealing the exterior portion with a valve.

A pressure within an external portion may be monitored with a gauge. A pressure within an external portion may be continuously monitored or periodically monitored. Monitoring a pressure within an external portion may be useful to monitor an applied pressure, such as an applied pneumatic challenge. It may be beneficial to understand a pressure being applied by an interrogation device, for example, to prevent over pressurization of a patient ear.

A device 100' may comprise a seal 180' coupled to an exterior portion 125'. In a clinical setting, an interrogation device may comprise a seal to a subject orifice. For example, a speculum of an otoscope may comprise a size and shape to fit within a biological ear canal, such as an ear canal of an adult or an infant subject. Seal 180' may simulate a biological seal between an interrogation device and a subject orifice. In some cases, an external pressure gauge may be used to monitor a quality of a seal when an interrogation device is in place or in use.

Figure 1C:
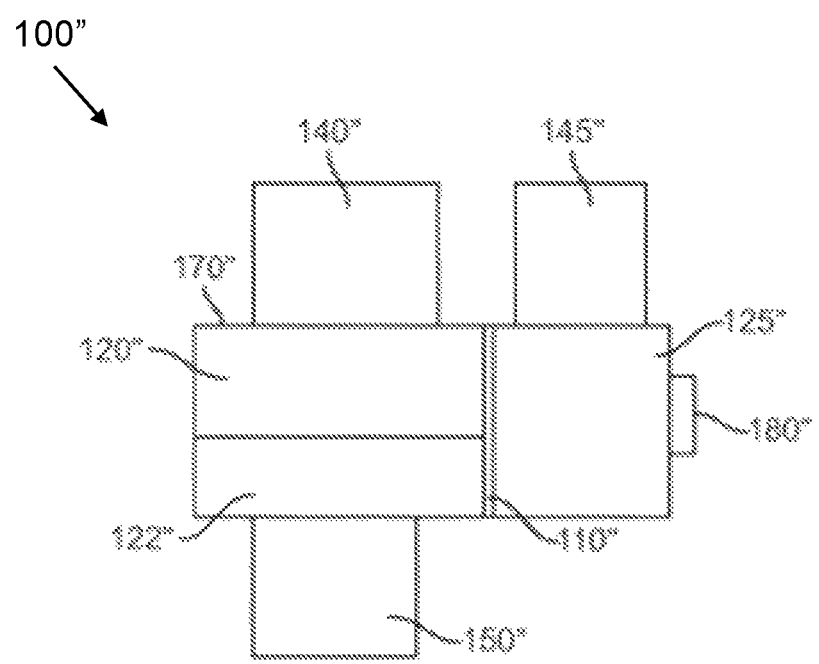
FIG. 1C illustrates a schematic of a device for modeling properties of an ear comprising an interior portion an exterior portion with a seal, in accordance with some embodiments.

FIG. 1C illustrates a schematic of device 100" for modeling properties of an ear comprising an interior portion an exterior portion with a seal, in accordance with some embodiments. The device may comprise housing 170". Housing 170" may comprise interior portion 120". Housing 170" may comprise a fluid injector 150" coupled to the housing. Housing 170" may comprise an internal air valve or an internal air pump 140" coupled to the housing. A housing may comprise a main chamber divided by an artificial tympanic membrane and comprising at least an interior and an exterior portion 125". Housing 170" may comprise an external air valve or an external air pump 145" coupled to the housing. Housing 170" may comprise a seal 180" coupled to the housing.

The example of FIG. 1C may comprise an artificial tympanic membrane 110" with a shape and a durometer of the artificial tympanic membrane is configured to mimic a presence of an ossicular chain. Membrane 110" may be used in combination with or in place of an elastic material (e.g. a mock ossicular chain) as described elsewhere herein.

A housing 170" may comprise an artificial tympanic membrane 110". Membrane 110" may comprise a material with properties which mimic biological tympanic membrane. For example, membrane 110" may mimic a tension or a shape of biological tympanic membrane. For example, a membrane 110" may be distended or retracted to mimic a biological tympanic membrane. A membrane may distend or retract to mimic a healthy state or a diseased state of an ear. A membrane may move in response to an applied pneumatic challenge. A rate of membrane movement in response to an applied pneumatic challenge may mimic a disease state or a healthy state of an ear. Membrane 110" may have shape which displays visual cues which mimic a visual appearance of biological tympanic membrane. For example, a surface of an artificial tympanic membrane may have visual shape of a malleus or an umbo or both. A tympanic membrane may have a reflectivity for ultrasound which mimics a biological ultrasound reflectivity.

The interior portion may comprise a liquid. A liquid volume 122" may be adjustable to simulate an amount of fluid behind a tympanic membrane. In some cases, a type of fluid may be adjustable to simulate properties of a biological fluid. For example, a type of fluid may be changed to raise or lower a viscosity of a fluid behind a membrane. Changing a viscosity of a fluid may alter a motion or a rate of motion of a tympanic membrane. For example, a more viscous fluid may reduce the effective elasticity of a tympanic membrane. In some cases, the interior portion comprises a fluid injector or an opening for a fluid injector. The fluid injector may be used to raise or lower a volume of a liquid. The fluid injector may be used to change a type of liquid.

In some cases, the type of liquid may be water. In some cases, the type of fluid may be a solution. In some cases, a type of fluid may be an aqueous solution. A viscosity of an aqueous solution may be changed by controlling an amount of a solute in a solvent. For example, sodium chloride, potassium iodide, sugar, etc. may be added to water to change a viscosity. In some cases, the type of liquid may be honey. In some cases, a type of liquid may be an oil, such as olive oil, linseed oil, castor oil, motor oil, mineral oil, silicone oil, etc. In some cases, a type of liquid may be a suspension of two immiscible liquids. In some cases, a type of fluid may be a suspension of an oil and water. In some cases, a fluid may be a paste, a gel, or another semisolid. In some cases, a fluid may be a viscoelastic polymer. A viscosity of a fluid may be changed with temperature. For example, at room temperature a viscosity of a fluid may be varied between 100 microPascal seconds, e.g. a light fluid, to 5000 Pascal seconds, e.g., honey.

Interior portion 120" may comprise an adjustable air volume. The air volume may be adjusted to simulate a pressure behind a tympanic membrane. A pressure behind a tympanic membrane may adjust a motion or a rate of motion of a tympanic membrane. For example, a higher pressure behind a tympanic membrane may reduce a motion or a rate of motion of a tympanic membrane. In some cases, the interior portion comprises an internal air valve. A device 100" may comprise an internal air pump. A device 100" may comprise an opening for an internal air valve. A device 100" may comprise an opening for an internal air pump. In some case, the interior portion comprises an internal pressure gauge or an opening for an internal pressure gauge. Pressure within an interior portion may be regulated by a pump. Pressure with an interior portion may be regulated by raising or lower the pressure with a pump and sealing the interior portion with a valve. A pressure within an interior portion may be monitored with a gauge. A pressure within an interior portion may be continuously monitored or periodically monitored.

In some cases, a type of a gas may be air. A gas may comprise nitrogen, oxygen, helium, hydrogen, carbon dioxide, helium, krypton, argon, etc., and any combination thereof. A gas may comprise an inert gas. A gas may comprise an elemental gas. A pressure of gas may be varied from several millitorr to 100 kilotorr. Biological ear pressures may typically be about 760. Torr.

A device 100" may comprise an exterior portion 125" coupled to an exterior surface of the artificial tympanic membrane. Exterior portion 125" may comprise an adjustable air volume or pressure. The air volume or pressure may be adjusted to simulate an applied pressure to a tympanic membrane. A pressure applied to a tympanic membrane may be a pneumatic challenge. For example, a pneumatic challenge may induce membrane movement which may be measured by an interrogation device, e.g., an otoscope. In some cases, the external portion comprises an external air valve. A device 100" may comprise an external air pump. A device 100" may comprise an opening for an external air valve. A device 100" may comprise an opening for an external air pump. In some case, the exterior portion comprises an external pressure gauge or an opening for an external pressure gauge. Pressure within an external portion may be regulated by a pump. Pressure with an exterior portion may be regulated by raising or lower the pressure with a pump and sealing the exterior portion with a valve.

A pressure within an external portion may be monitored with a gauge. A pressure within an external portion may be continuously monitored or periodically monitored. Monitoring a pressure within an external portion may be useful to monitor an applied pressure, such as an applied pneumatic challenge. It may be beneficial to understand a pressure being applied by an interrogation device, for example, to prevent over pressurization of a patient ear.

A device 100" may comprise a seal 180" coupled to an exterior portion 125". In a clinical setting, an interrogation device may comprise a seal to a subject orifice. For example, a speculum of an otoscope may comprise a size and shape to fit within a biological ear canal, such as an ear canal of an adult or an infant subject. Seal 180" may simulate a biological seal between an interrogation device and a subject orifice. In some cases, an external pressure gauge may be used to monitor a quality of a seal when an interrogation device is in place or in use.

Figure 2:
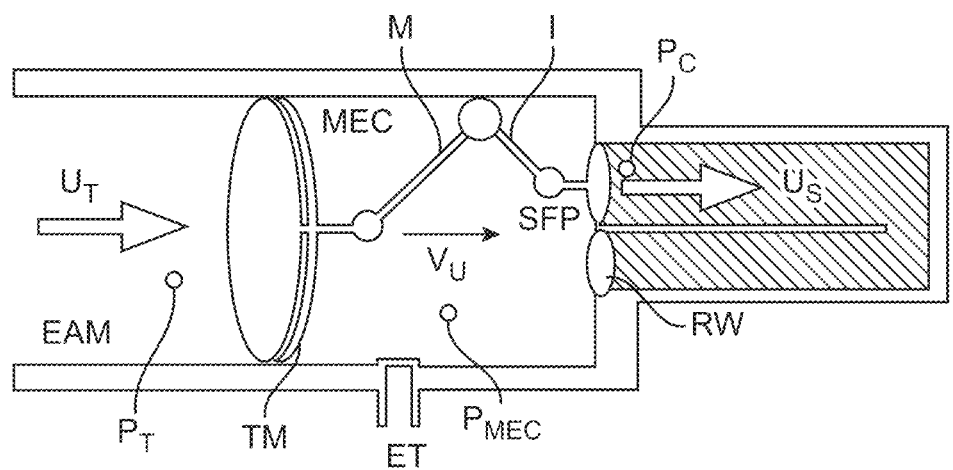
FIG. 2 illustrates some potential principles relevant to simulation of a membrane, in accordance with some embodiments.

FIG. 2 illustrates some potential principles relevant to simulation of a membrane, in accordance with some embodiments. FIG. 2 is an acoustico-mechanical schematic of the middle ear including the ear canal (EAM), Middle-ear cavity (MEC), Tympanic Membrane (TM), the ossicular linkage (M,I,SFP), and the fluid filled inner ear. The ossicular linkage, also ossicular chain, comprises the malleus M, incus I, and stapes footplate SFP. Also shown is the round window RW and Eustachian tube ET. With an external air pressure PT such as a pneumatic challenge or sound in the ear canal, the TM moves causing a volume displacement Vu and an accompanying pressure change within the middle ear PMEC. The back and forth movements of the TM also cause accompanying displacements in the ossicular chain and stapes footplate which induces a pressure change in the vestibule medial to the footplate Pc. The umbo is the sometimes-visible head of the malleus on the TM. For additional description of ear acoustico-mechanics, see for example, Acoustics of Speech & Hearing MIT 6.551J/HST.714J, http://web.mit.edu/6.551j/www/, which is incorporated herein by reference in its entirety.

OM is characterized by the presence of fluid behind the TM. Bacterial ear infections may be treated with antibiotics; however, viral ear infections may not be responsive to antibiotics. Bacterial versus viral OM are characterized by different types of effusions; however, an effusion behind a TM may not typically be visible from the external ear. Identification of the type of effusion may be aided by various interrogation devices which probe the movement of the tympanic membrane. Rather than biopsy of a subject TM or prescribing without diagnosis, these indirect methods may help identify infections correctly and earlier. For example, viral effusions are typically waterier (e.g. less viscous) than bacterial infections which may be gluier (e.g. more viscous).

Example of a method for probing membrane movement comprises applying a pneumatic challenge $U_T$ and monitoring membrane movement before and after that challenge. Monitoring a movement may be done by visual inspection or using more sophisticated methods such as using an ultrasound system or optical coherence tomography. These techniques are described in more detail elsewhere herein, for example in the section "Interrogation Device."

Probing membrane movement may comprise measurement of a membrane retraction or distention, measurement of a speed of movement, measurement of a damping time of membrane movement, measurement of a frequency of membrane movement, etc. A simple model of membrane movement in response to a pneumatic challenge is that of a simple harmonic oscillator. A spring force may be related to the elasticity of the TM, the compression of the cochlea (via the ossicular chain), the compression of air within the middle ear, etc. The damping of the oscillator may be related to the damping of the TM, air pressure equalization via the ET, pressure equalization within the cochlea, etc. The mass of the oscillator may be related to the mass of the TM, the mass of the fluid within the ear, and the mass of the ossicles. An accurate membrane simulation should capture many or all of these parameters using simple and adjustable parts.

Devices of the present disclosure may be selectively adjusted to produce movement properties which mimic a disease state. In some cases, at least one of a mass of the membrane, a tension of the elastomeric spring, a pressure in the interior portion, and an amount of fluid in the interior portion may be selectively controlled to approximate conditions within an ear. In some cases, an elastomeric spring may not be required. In some cases, a type or volume of a fluid and a pressure within an internal portion may be the adjustable parameters. A single membrane type may be used to controllably mimic multiple disease states. In some case, adjustment of one or more of the volume of fluid, the type of fluid, or the gas pressure changes a membrane deflection or a membrane movement to controllably mimic a disease state of an ear. In some cases, adjustment of the type of fluid comprises varying a viscosity of fluid. In some cases, the movement of the artificial tympanic membrane is adjustable according to a set of ordinal values or to a continuous scale. In some cases, adjustment of one or more of the volume of fluid, the type of fluid, or the gas pressure changes a rate of the membrane movement to controllably mimic a disease state of an ear.

Figure 3A:
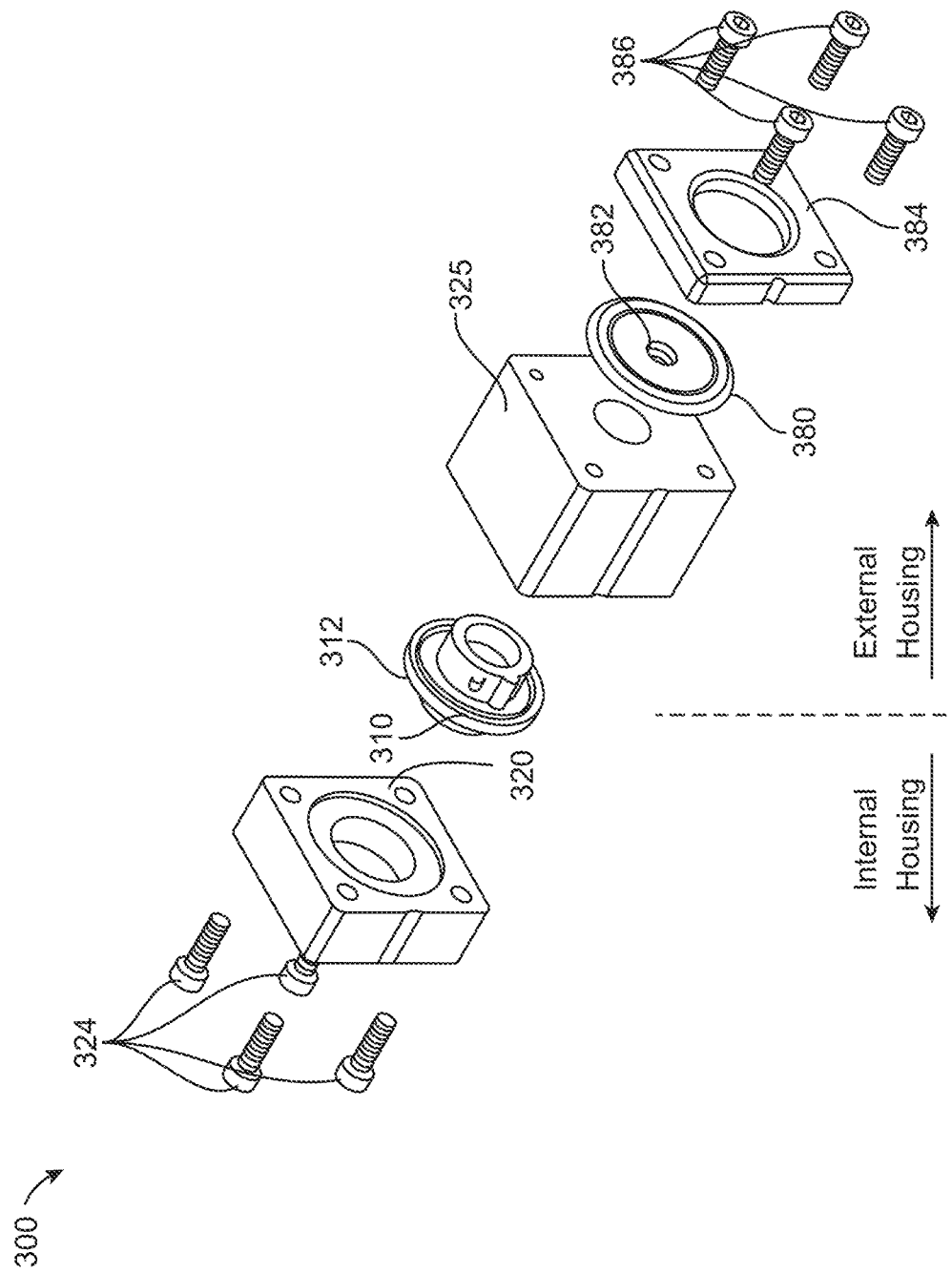
FIG. 3A illustrates an exploded view of an example device for modeling properties of an ear comprising an interior portion and an exterior portion with a seal, in accordance with some embodiments.
Figure 3B:
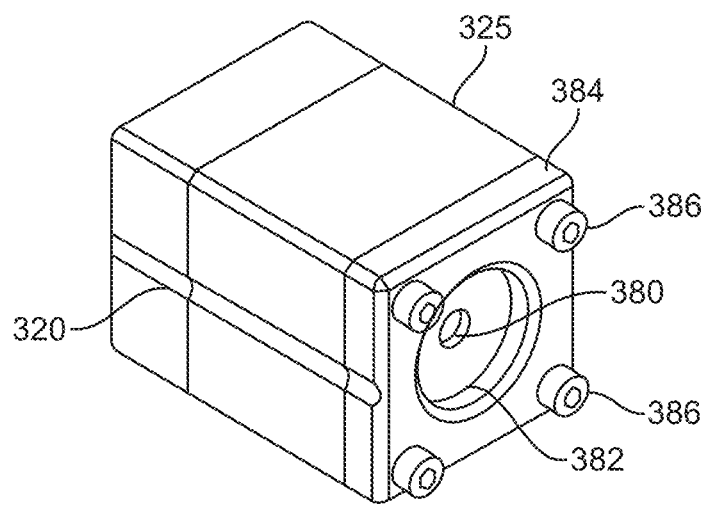
FIG. 3B illustrates an exterior isometric view of the example device of FIG. 3A for modeling properties of an ear, in accordance with some embodiments.
Figure 3C:
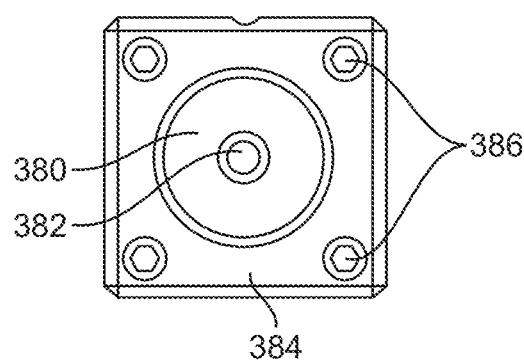
FIG. 3C illustrates an exterior front view of the example device of FIG. 3A for modeling properties of an ear, in accordance with some embodiments.

FIG. 3A illustrates an exploded view of an example device 300 for modeling properties of an ear comprising an interior portion and an exterior portion with a seal, accordance with some embodiments. FIG. 3B illustrates an exterior isometric view of the example device of FIG. 3A for modeling properties of an ear, in accordance with some embodiments. FIG. 3C illustrates an exterior front view of the example device of FIG. 3A for modeling properties of an ear, in accordance with some embodiments. Device 300 may comprise an example implementation the schematic device 100" presented in FIG. 1C.

The device may comprise a housing. The housing may comprise interior portion 320. Housing may comprise an opening for a fluid injector. The housing may comprise an opening for an internal air valve or an internal air pump coupled to the interior portion 320. A housing may comprise a main chamber divided by an artificial tympanic membrane and comprising at least an interior 320 and an exterior portion 325. The exterior portion may comprise opening for an external air valve or an external air pump coupled to the exterior portion. The device may comprise a seal 380 coupled to the housing.

Device 300 may comprise an artificial tympanic membrane 310 with a shape and a durometer of the artificial tympanic membrane is configured to mimic a presence of an ossicular chain. Membrane 310 may be used in combination with or in place of an elastic material (e.g., a mock ossicular chain) as described elsewhere herein. As shown membrane 310 may comprise a seal 312 to aid in pressure separation between the interior portion and the exterior portion. Membrane 310 may comprise orienting features.

Device 300 may comprise an artificial tympanic membrane 310. Membrane 310 may comprise a material with properties which mimic biological tympanic membrane. For example, membrane 310 may mimic a tension or a shape of biological tympanic membrane. For example, a membrane 310 may be distended or retracted to mimic a biological tympanic membrane. A membrane may distend or retract to mimic a healthy state or a diseased state of an ear. A membrane may move in response to an applied pneumatic challenge. A rate of membrane movement in response to an applied pneumatic challenge may mimic a disease state or a healthy state of an ear. Membrane 310 may have shape which displays visual cues which mimic a visual appearance of biological tympanic membrane. For example, a surface of an artificial tympanic membrane may have visual shape of a malleus or an umbo or both. A tympanic membrane may have a reflectivity for ultrasound which mimics a biological ultrasound reflectivity.

The interior portion 320 may comprise a liquid. A liquid volume may be adjustable to simulate an amount of fluid behind a tympanic membrane. In some cases, a type of fluid may be adjustable to simulate properties of a biological fluid. For example, a type of fluid may be changed to raise or lower a viscosity of a fluid behind a membrane. Changing a viscosity of a fluid may alter a motion or a rate of motion of a tympanic membrane. For example, a more viscous fluid may reduce the effective elasticity of a tympanic membrane. In some cases, the interior portion comprises an opening for a fluid injector. The fluid injector may be used to raise or lower a volume of a liquid. The fluid injector may be used to change a type of liquid.

In some cases, the type of liquid may be water. In some cases, the type of fluid may a solution. In some cases, a type of fluid may be an aqueous solution. A viscosity of an aqueous solution may be changed by controlling an amount of a solute in a solvent. For example, sodium chloride, potassium iodide, sugar, etc. may be added to water to change a viscosity. In some cases, the type of liquid may be honey. In some cases, a type of liquid may be an oil, such as olive oil, linseed oil, castor oil, motor oil, mineral oil, silicone oil, etc. In some cases, a type of liquid may be a suspension of two immiscible liquids. In some cases, a type of fluid may be a suspension of an oil and water. In some cases, a fluid may be a paste, a gel, or another semisolid. In some cases, a fluid may be a viscoelastic polymer. A viscosity of a fluid may be changed with temperature. For example, at room temperature a viscosity of a fluid may be varied between 100 microPascal seconds, e.g. a light fluid, to 1000 Pascal seconds, e.g., tar.

Interior portion 320 may comprise an adjustable air volume. The air volume may be adjusted to simulate a pressure behind a tympanic membrane. A pressure behind a tympanic membrane may adjust a motion or a rate of motion of a tympanic membrane. For example, a higher pressure behind a tympanic membrane may reduce a motion or a rate of motion of a tympanic membrane. In some cases, the interior portion comprises an internal air valve. Device 300 may comprise an opening for an internal air pump. Device 300 may comprise an opening for an internal air valve. In some case, the interior portion comprises an opening for an internal pressure gauge. Pressure within an interior portion may be regulated by a pump. Pressure with an interior portion may be regulated by raising or lower the pressure with a pump and sealing the interior portion with a valve. A pressure within an interior portion may be monitored with a gauge. A pressure within an interior portion may be continuously monitored or periodically monitored.

In some cases, a type of a gas may be air. A gas may comprise nitrogen, oxygen, helium, hydrogen, carbon dioxide, helium, krypton, argon, etc., and any combination thereof. A gas may comprise an inert gas. A gas may comprise an elemental gas. A pressure of gas may be varied from several millitorr to 100 kilotorr. Biological ear pressures may typically be about 760 Torr.

The interior portion 320 may be affixed to exterior portion by attachment device 324. The interior portion and the exterior portion may be attached by screws, bolts, a screw fit, a snap fit, etc. The interior portion and the exterior portion may be fluidically and pneumatically sealed from one another.

A device 300 may comprise an exterior portion 325 coupled to an exterior surface of the artificial tympanic membrane. Exterior portion 325 may comprise an adjustable air volume or pressure. The air volume or pressure may be adjusted to simulate an applied pressure to a tympanic membrane. A pressure applied to a tympanic membrane may be a pneumatic challenge. For example, a pneumatic challenge may induce membrane movement which may be measured by an interrogation device, e.g., an otoscope. In some cases, the external portion comprises an opening for an external air valve. A device 300 may comprise an opening for an external air pump. In some case, the exterior portion comprises an opening for an external pressure gauge. Pressure within an external portion may be regulated by a pump. Pressure with an exterior portion may be regulated by raising or lower the pressure with a pump and sealing the exterior portion with a valve.

A pressure within an external portion may be monitored with a gauge. A pressure within an external portion may be continuously monitored or periodically monitored. Monitoring a pressure within an external portion may be useful to monitor an applied pressure, such as an applied pneumatic challenge. It may be beneficial to understand a pressure being applied by an interrogation device, for example, to prevent over pressurization of a patient ear.

A device 300 may comprise a seal 380 coupled to an exterior portion 325. In a clinical setting, an interrogation device may comprise a seal to a subject orifice. For example, a speculum of an otoscope may comprise a size and shape to fit within a biological ear canal, such as an ear canal of an adult or an infant subject. Seal 380 may simulate a biological seal between an interrogation device and a subject orifice. In some cases, an external pressure gauge may be used to monitor a quality of a seal when an interrogation device is in place or in use.

Seal 380 may comprise an opening 382 for an interrogation device to be inserted into. Seal 380 may form a fluidic and pneumatic seal between the exterior portion and an exterior of the device. Seal 380 may be attached to the exterior portion by face plate 384. The face plate 384 may be affixed to the exterior portion by attachment devices 386. The face plate and the exterior portion may be attached by screws, bolts, a screw fit, a snap fit, etc.

Figure 4:
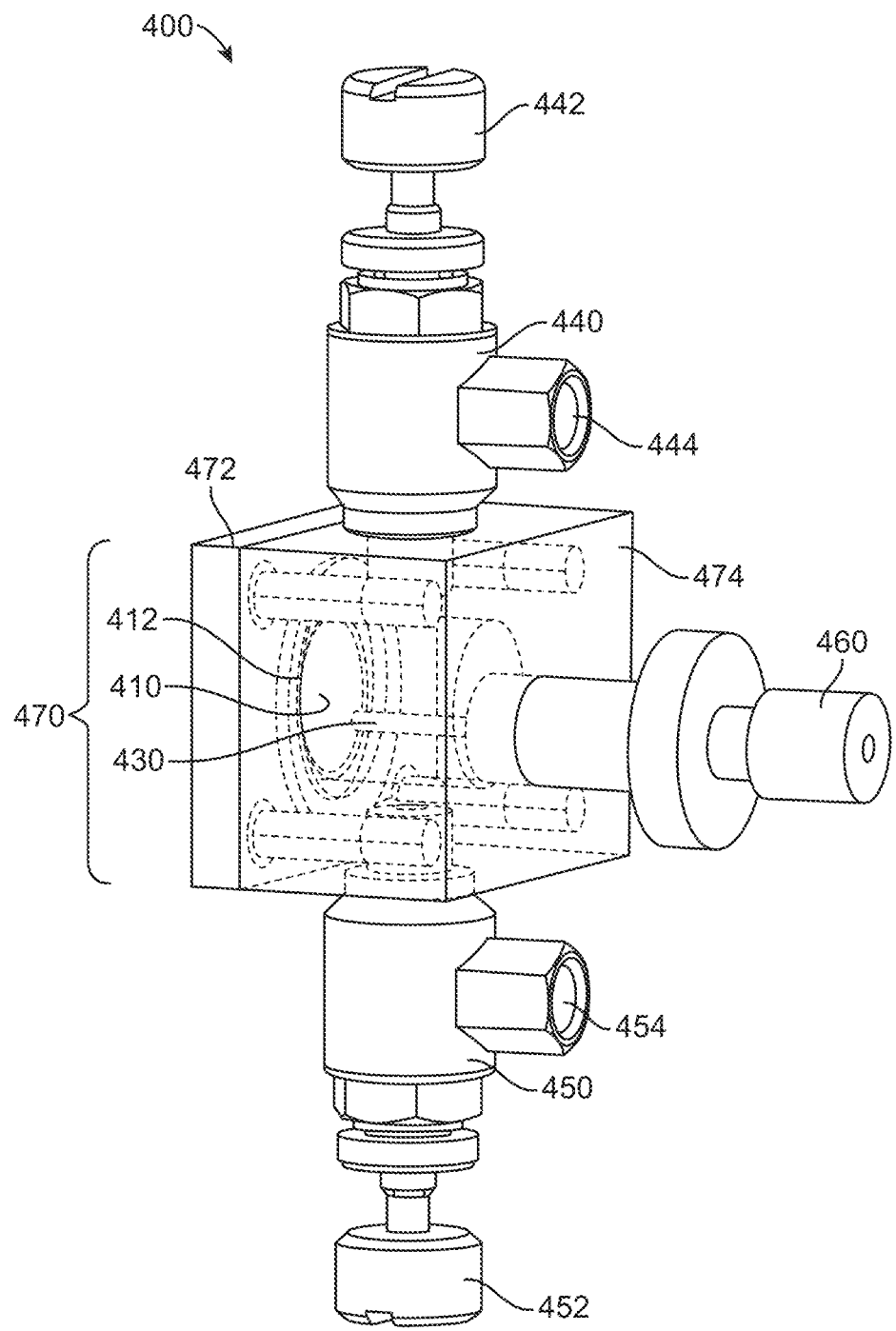
FIG. 4 illustrates a transparent isometric view of an example device comprising an interior portion with a mock ossicular chain, in accordance with some embodiments.

FIG. 4 illustrates a transparent isometric view of an example device comprising an interior portion with a mock ossicular chain, in accordance with some embodiments. Device 400 may comprise an example implementation the schematic device 100 presented in FIG. 1A. The device may comprise housing 470. Housing 470 may comprise an interior portion. Housing 470 may comprise an elastic material 430, which may act as a mock ossicular chain. Housing 470 may comprise a fluid injector connection 450 coupled to the housing. Housing 470 may comprise an air valve connection 440 coupled to the housing. A housing may comprise a main chamber divided by an artificial tympanic membrane and comprising at least an interior and, optionally, an exterior portion.

A housing 470 may comprise an artificial tympanic membrane 410. Membrane 410 may comprise a material with properties which mimic biological tympanic membrane. For example, membrane 410 may mimic a tension or a shape of biological tympanic membrane. For example, a membrane 410 may be distended or retracted to mimic a biological tympanic membrane. A membrane may distend or retract to mimic a healthy state or a diseased state of an ear. A membrane may move in response to an applied pneumatic challenge. A rate of membrane movement in response to an applied pneumatic challenge may mimic a disease state or a healthy state of an ear. Membrane 410 may have a shape which displays visual cues which mimic a visual appearance of biological tympanic membrane. For example, a surface of an artificial tympanic membrane may have visual shape of a malleus or an umbo or both. A tympanic membrane may have a reflectivity for ultrasound which mimics a biological ultrasound reflectivity.

As shown, membrane 410 comprises a seal 412 aid in pressure separation between the interior portion and an exterior of the device. A faceplate 472 may interface with an interior portion of the housing 474. The interior portion and the faceplate may be attached by screws, bolts, a screw fit, a snap fit, etc.

The interior portion may comprise a liquid. A liquid volume may be adjustable to simulate an amount of fluid behind a tympanic membrane. In some cases, a type of fluid may be adjustable to simulate properties of a biological fluid. For example, a type of fluid may be changed to raise or lower a viscosity of a fluid behind a membrane. Changing a viscosity of a fluid may alter a motion or a rate of motion of a tympanic membrane. For example, a more viscous fluid may reduce the effective elasticity of a tympanic membrane. In some cases, the interior portion comprises an opening for a fluid injector. The interior portion may comprise a fluid injector connection 450. The interior portion may comprise a valve 452 and a fluid exit 454. The fluid injector may be used to raise or lower a volume of a liquid. The fluid injector may be used to change a type of liquid.

In some cases, the type of liquid may be water. In some cases, the type of fluid may a solution. In some cases, a type of fluid may be an aqueous solution. A viscosity of an aqueous solution may be changed by controlling an amount of a solute in a solvent. For example, sodium chloride, potassium iodide, sugar, etc. may be added to water to change a viscosity. In some cases, the type of liquid may be honey. In some cases, a type of liquid may be an oil, such as olive oil, linseed oil, castor oil, motor oil, mineral oil, silicone oil, etc. In some cases, a type of liquid may be a suspension of two immiscible liquids. In some cases, a type of fluid may be a suspension of an oil and water. In some cases, a fluid may be a paste, a gel, or another semisolid. In some cases, a fluid may be a viscoelastic polymer. A viscosity of a fluid may be changed with temperature. For example, at room temperature a viscosity of a fluid may be varied between 100 microPascal seconds, e.g. a light fluid, to 5000 Pascal seconds, e.g., honey.

Interior portion 474 may comprise an adjustable air volume. The air volume may be adjusted to simulate a pressure behind a tympanic membrane. A pressure behind a tympanic membrane may adjust a motion or a rate of motion of a tympanic membrane. For example, a higher pressure behind a tympanic membrane may reduce a motion or a rate of motion of a tympanic membrane. In some cases, the interior portion comprises an internal air valve. A device 400 may comprise an internal air pump connection 440. A device 400 may comprise an opening for an internal air valve 442 and an exit 444. In some case, the interior portion comprises an opening for an internal pressure gauge. Pressure within an interior portion may be regulated by a pump. Pressure with an interior portion may be regulated by raising or lower the pressure with a pump and sealing the interior portion with a valve. A pressure within an interior portion may be monitored with a gauge. A pressure within an interior portion may be continuously monitored or periodically monitored.

In some cases, a type of a gas may be air. A gas may comprise nitrogen, oxygen, helium, hydrogen, carbon dioxide, helium, krypton, argon, etc., and any combination thereof. A gas may comprise an inert gas. A gas may comprise an elemental gas. A pressure of gas may be varied from several millitorr to 100 kilotorr. Biological ear pressures may typically be about 760 Torr.

In some cases, the interior portion 474 may comprise an elastic material 430 coupled to an artificial tympanic membrane. In some cases, the interior portion comprises a mock ossicular chain coupled to the tympanic membrane. In some case, an elastic material coupled to an artificial tympanic membrane is a spring, e.g., an elastomeric spring. In some cases, an elastic material coupled to an artificial tympanic membrane has a controllable tension. A mock ossicular may have a controllable tension. FIG. 4 shows a spring adjustor 460 coupled to elastic material 430. The spring adjustor may control a tension to adjust an elasticity of an artificial tympanic membrane 410.

Artificial Tympanic Membrane

Figure 5A:
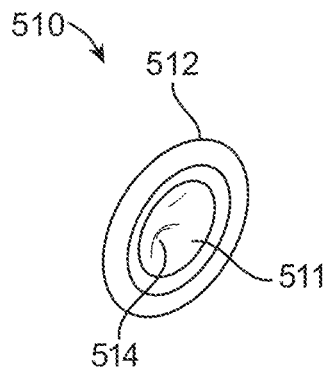
FIG. 5A, FIG. 5B, and FIG. 5C show isometric, front, and side views, respectively, of an artificial tympanic membrane, in accordance with some embodiments.
Figure 5B:
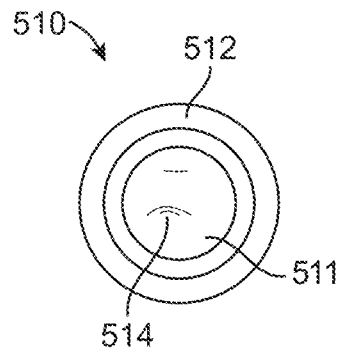
Figure 5C:
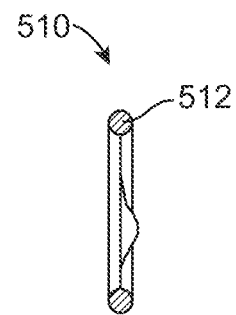

FIG. 5A, FIG. 5B, and FIG. 5C show isometric, front, and side views, respectively, of an artificial tympanic membrane, in accordance with some embodiments. Membrane 510 may comprise a flexible surface 511. Membrane 510 may comprise a material with properties which mimic biological tympanic membrane. For example, membrane 510 may mimic a tension or a shape of biological tympanic membrane. For example, a membrane 510 may be distended or retracted to mimic a biological tympanic membrane. A membrane may distend or retract to mimic a healthy state or a diseased state of an ear. A membrane may move in response to an applied pneumatic challenge.

A membrane 510 may comprise a shape and/or a durometer configured to mimic a presence of an ossicular chain. Membrane 510 may be used in combination with or in place of an elastic material (e.g., a mock ossicular chain) as described elsewhere herein. A rate of membrane movement in response to an applied pneumatic challenge may mimic a disease state or a healthy state of an ear. Membrane 510 may have shape which displays visual cues which mimic a visual appearance of biological tympanic membrane. For example, a surface of an artificial tympanic membrane may have visual shape of a malleus or an umbo or both. A tympanic membrane may have a reflectivity for ultrasound which mimics a biological ultrasound reflectivity.

Various parameters may be adjusted to approximate conditions within the ear, for example, diseased states or healthy states. In some cases, one or more of a mass of the membrane, a damping of the elastomeric spring, a spring rate, a pressure in the interior of the main chamber, and an amount of fluid or a type of fluid in the interior of the main chamber may be selectively controlled to approximate conditions within an ear.

The membrane may comprise a flexible material. The membrane may comprise an elastomer. The elastomer may comprise natural rubber, neoprene rubber, buna-s, buna-n, an elastomeric polymer, silicone rubber, polyisoprene, polybutadiene, chloroprene, butyl rubber, styrene rubber, nitrile rubber, ethylene propylene rubber, epichlorohydrin rubber, polyacrylic rubber, fluorosilicone rubber, fluoroelastomers, perfluoroelastomers, polyether block amides, chlorosulfonated polyethylene, ethylene-vinyl acetate, etc. The membrane may comprise silicone. In some cases, a membrane comprises a seal 512 to aid in attachment to a device of the present disclosure.

Figure 5D:
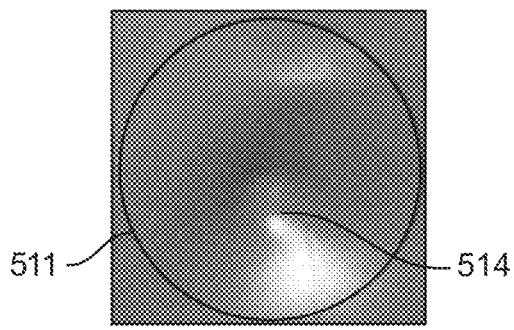
FIG. 5D is an image of an exterior surface of an example artificial tympanic membrane of the present disclosure.

FIG. 5D is an image of an exterior surface 511 of an example artificial tympanic membrane of the present disclosure. The visual appearance of the tympanic membrane may be an important consideration, as otoscopes may be often aligned by eye. Membranes of the present disclosure may be designed to exhibit one or more visual cues. For example, the membrane may exhibit at least partially a shape 514 of an umbo or a malleus.

In some cases, a membrane of the present disclosure has a shape which exhibits an optical reflection from the artificial tympanic membrane surface to enable location of the artificial tympanic membrane and alignment of an otoscope. In some cases, a membrane of the present disclosure exhibits a cone of light. In some cases, the optical reflection is exhibited on an anterior inferior quadrant of the artificial tympanic membrane.

The cone of light, or light reflex, is a visible phenomenon which may occur during visual examination of the tympanic membrane. Shining light onto the tympanic membrane may cause a cone-shaped reflection of light to appear. The apex of the cone is at the most depressed part of the tympanic membrane, the umbo. This may be located in the anterior inferior quadrant of the tympanic membrane. The cone of light may be used as an alignment aid during examination of the tympanic membrane. In an ear, a user may align a light source within an ear canal so that a cone of light is visible. In FIG. 5D, the cone of light is shown as bright spot near umbo 514.

Air and Liquid Subsystem

Figure 6:
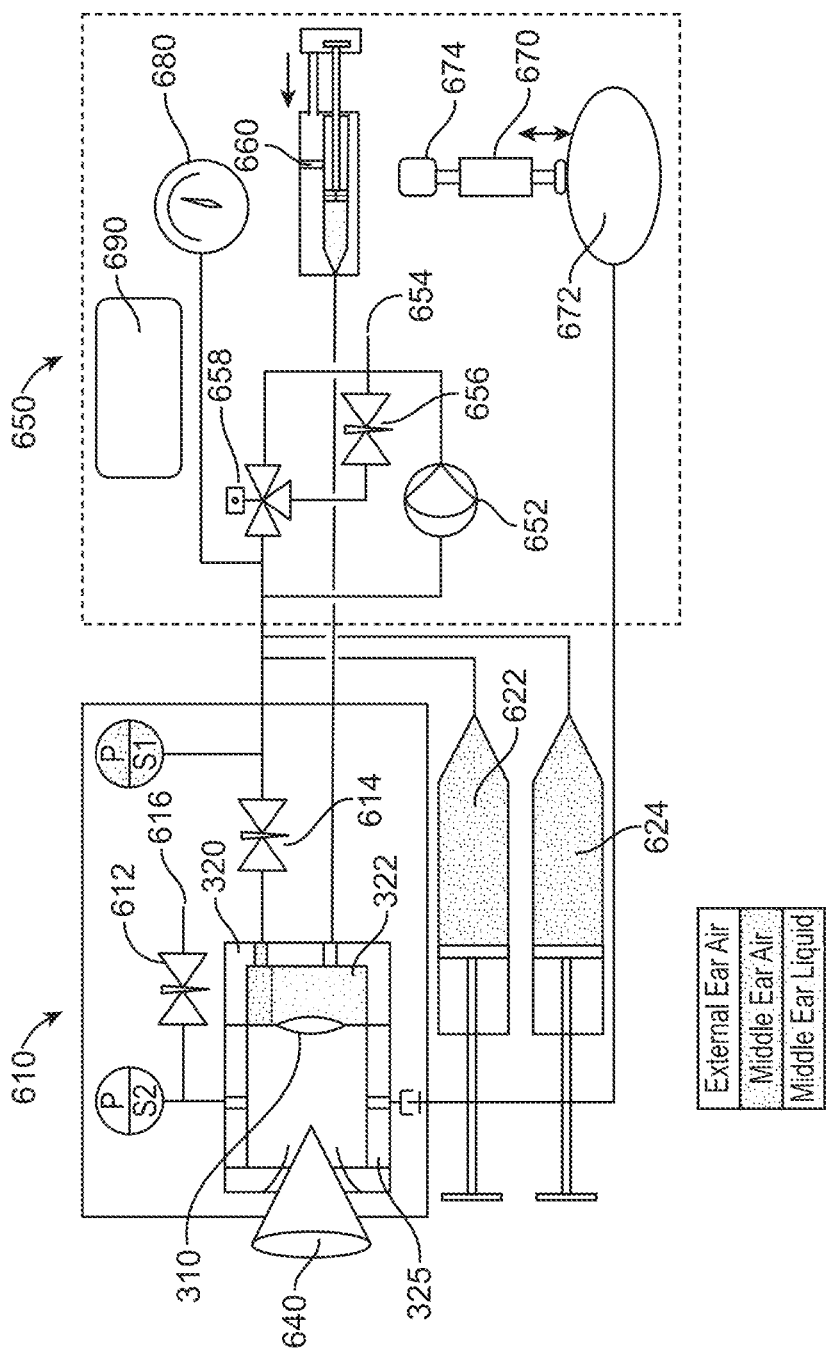
FIG. 6 is a diagram of an example air and liquid subsystem for a device for modeling properties of an ear, in accordance with some embodiments.

FIG. 6 is a diagram of an example air and liquid subsystem for a device for modeling properties of an ear, in accordance with some embodiments. The example air and liquid subsystem may be used in combination with any variation, embodiment, or example of a device for modeling properties of an ear disclosed herein. As shown, the air and liquid subsystem comprise a control unit 650 and measurement unit 610. The measurement unit 610 may comprise an embodiment, variation, or example of a device for modeling properties of an air. The device may comprise housing. A housing may comprise a main chamber divided by an artificial tympanic membrane 310 and comprising at least an interior 320 and an exterior portion 325.

The measurement unit 610 may comprise controls for components of interior portion 320. The internal portion may comprise an opening for a fluid injector 660. The housing may comprise an opening for an internal air valve 614. As shown, a first valve 614 may separate the measurement unit from the control unit. A digital pressure gauge P/S1 may be fluidically connected to the air handling line. One or more syringes 622 and 624 may be fluidically connected to the internal air system for fine pressure control.

The measurement unit 610 may comprise controls for components of exterior portion 325. The exterior portion 325 may comprise an opening for an external air valve 612. The external air value 612 may act as a vent valve. A digital pressure gauge P/S2 may be fluidically connected to the external air handling line. As shown, an external air pump 672 may be coupled to the exterior portion. The device may comprise a seal coupled to the housing. Also shown is an interrogation device 640 within the seal.

Figure 7:
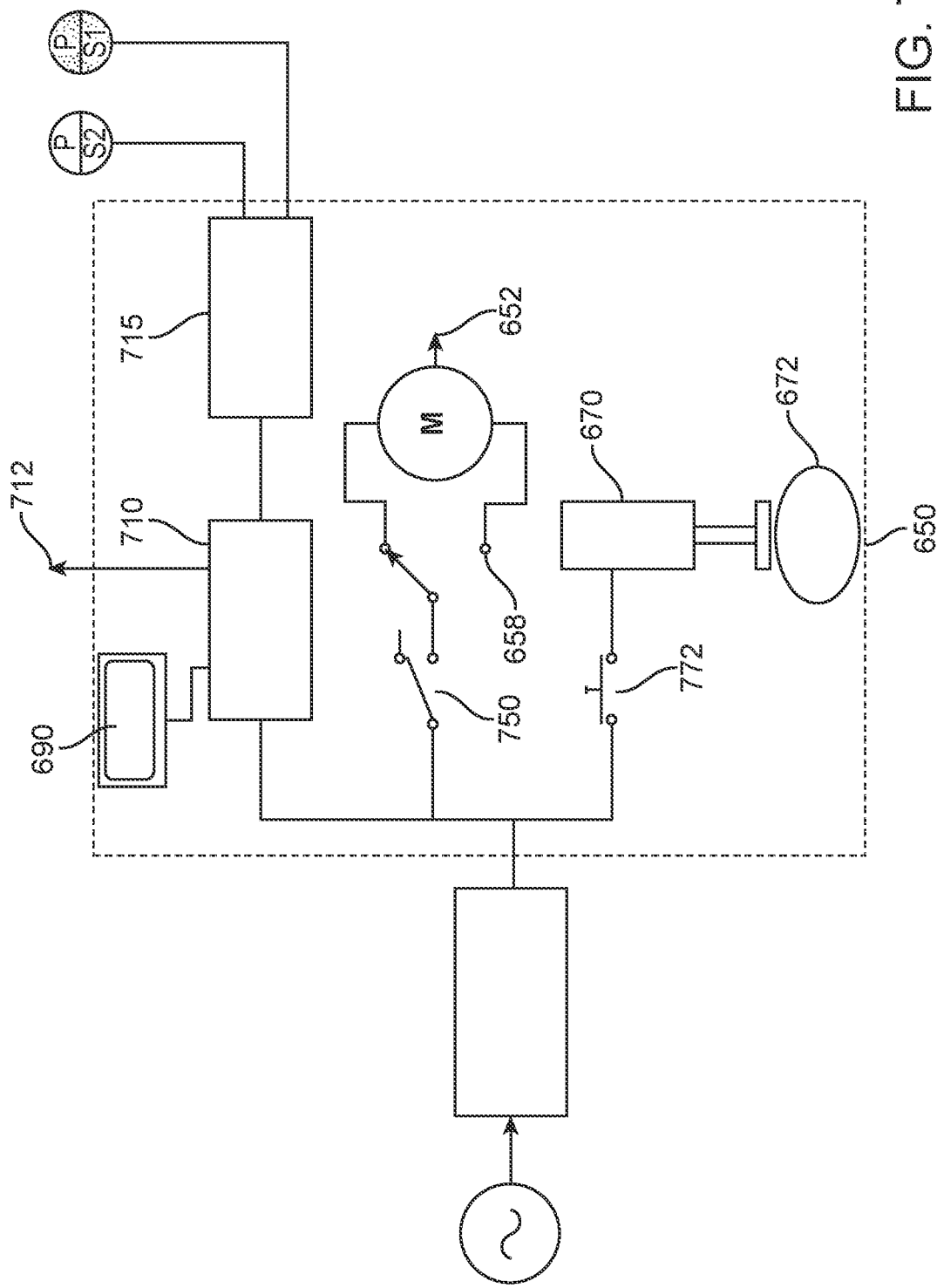
FIG. 7 is a diagram of an example electrical subsystem for a device for modeling properties of an ear, in accordance with some embodiments.

The control unit 650 may comprise an electrical subsystem, described in more detail with respect to FIG. 7. The control unit may comprise an internal air pump 652 coupled to the interior portion 320. The internal air pump may be a micro-diaphragm pump. The internal air line may comprise vent 654 and vent valve 656. The internal air line may comprise directional control 658. The control unit may also comprise a gauge 680 on the internal air line. The gauge may be visible to user. The gauge may be an analogue gauge. The control unit may comprise a fluid injector 660 coupled to the internal fluid line. The fluid injector may comprise a syringe pump. The control unit may comprise an external air pump 672. The external air pump may comprise a bulb with a bulb compressor 670 and control 674. The bulb compressor may comprise a solenoid. The bulb may mimic the action of a manually controlled pneumatic otoscope.

FIG. 7 is a diagram of an example electrical subsystem for a device for modeling properties of an ear, in accordance with some embodiments. Digital pressure gauge P/S1 and digital pressure gauge P/S2 may provide electrical signal to an analogue to digital converter (DAC) 715. The DAC may provide at least two channel output to a digital processing device 710. The digital processing device may be a microprocessor, such as an Arduino microprocessor. The digital processing device may be connected to one or more secondary processors through output 712, such as a USB or an ethernet port. The digital processing device 710 may be connected to a display visible 690 to a user.

The processor may be connected to control various aspects of the devices and methods disclosed herein. Pump 652 may comprise motor M. Motor M may be controlled by power switch 750 and directional control 658. The processor may be configured to control the operation of motor M, power switch 750, and directional control 658. The processor may be configured to control the operation of solenoid control switch 772 to move solenoid 670 to compress bulb 672.

Figure 8:
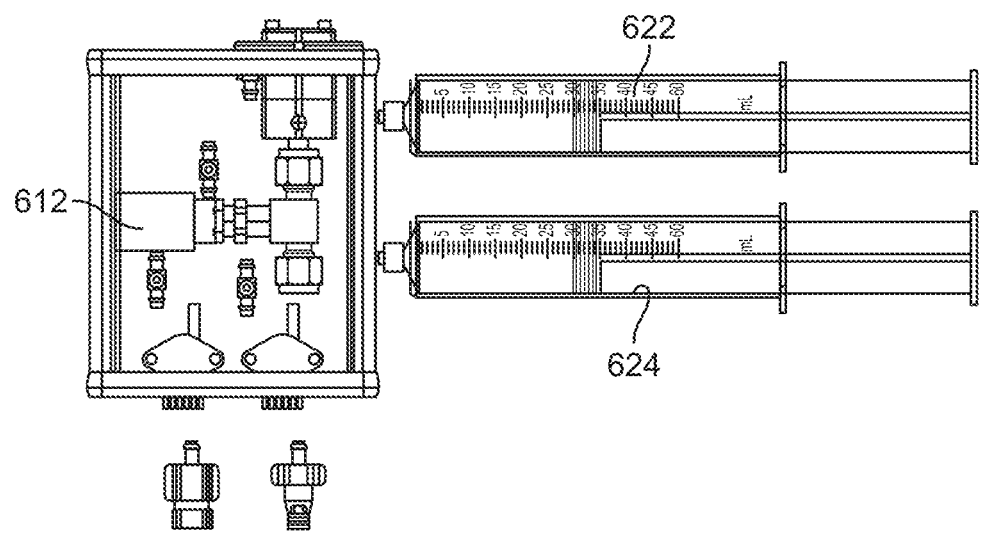
FIG. 8 illustrates a top view of an air and liquid subsystem for a device for modeling properties of an ear, in accordance with some embodiments.
Figure 8:
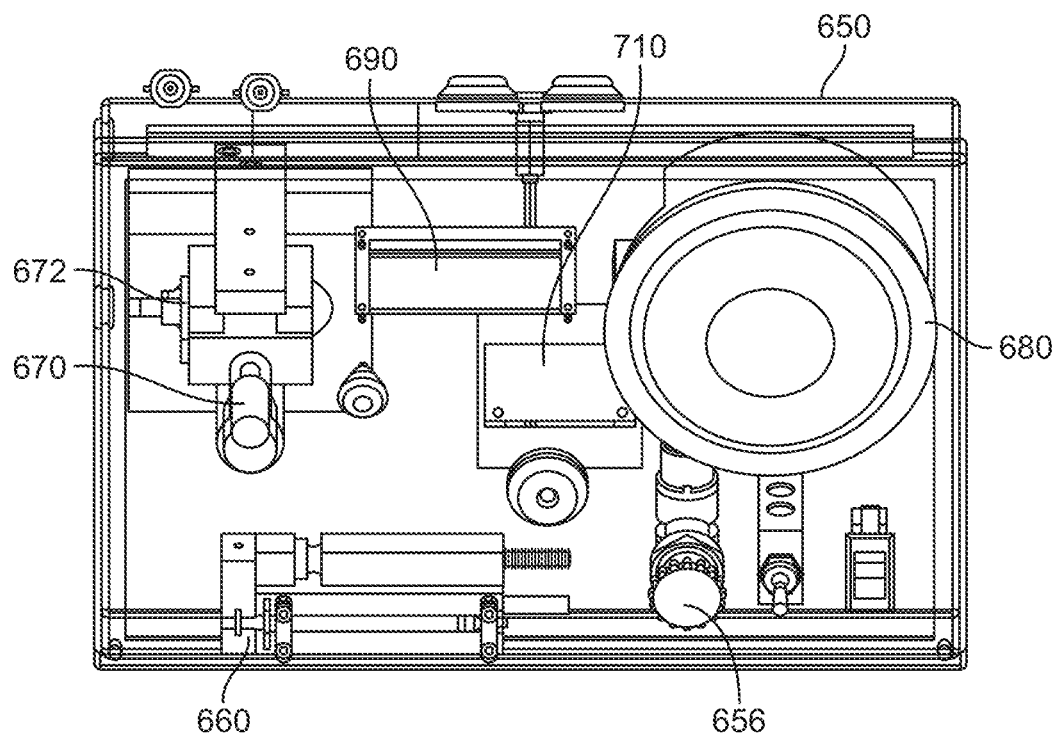

FIG. 8 illustrates a top view of an air and liquid subsystem for a device for modeling properties of an ear, in accordance with some embodiments. The lower portion of FIG. 8 shows control unit 650. Control unit 650 may comprise a digital processing device 710. The digital processing device 710 may be connected to a display visible 690 to a user. The control unit may also comprise a gauge 680 on the internal air line, which may be visible on an external surface of the control unit. The control unit may comprise an external air pump 672. The external air pump may comprise a bulb with a bulb compressor 670 and control 674. The control unit may comprise a fluid injector 660 coupled to the internal fluid line. The upper portion of FIG. 8 shows external air value 612 and one or more syringes 622 and 624.

Figure 9:
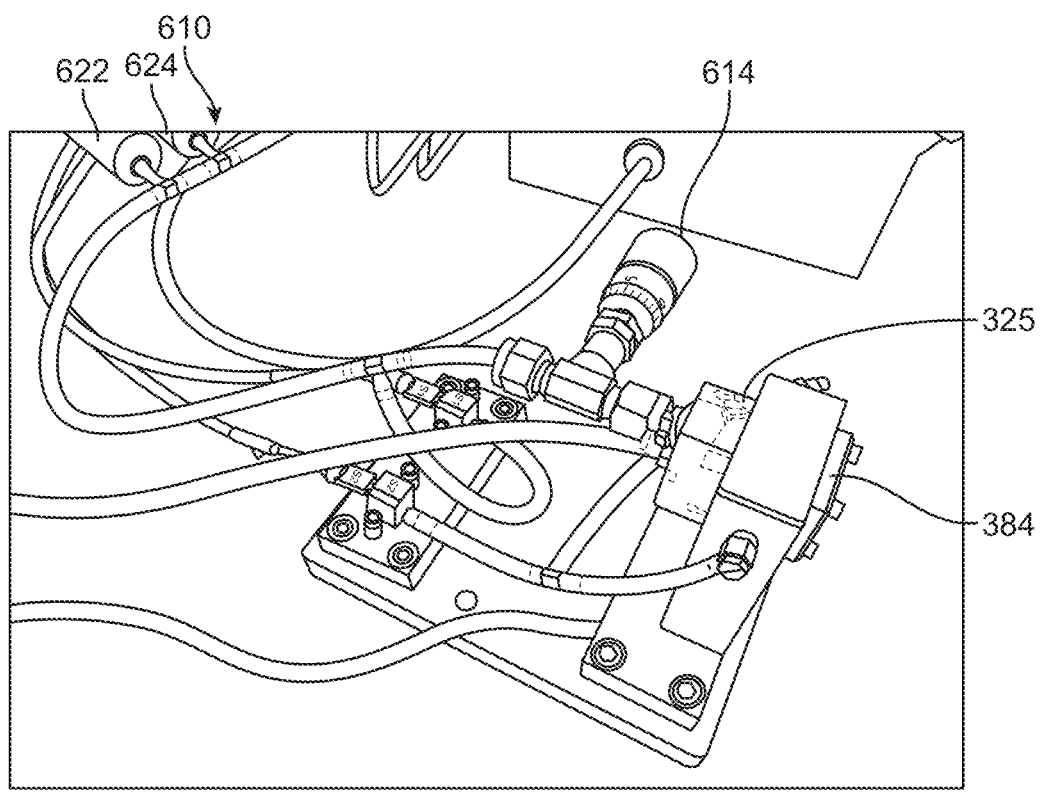
FIG. 9 is a photograph of a device for modeling properties of an ear connected to an air and liquid subsystem, in accordance with some embodiments.

FIG. 9 illustrates a measurement unit of a device for modeling properties of an ear connected to an air and liquid subsystem, in accordance with some embodiments. The measurement unit 610 may comprise a stand for a device of the present disclosure. The measurement unit may comprise digital pressure gauge P/S1 and digital pressure gauge P/S2. The measurement unit may comprise internal air valve 614.

Artificial External Ear

Figure 10:
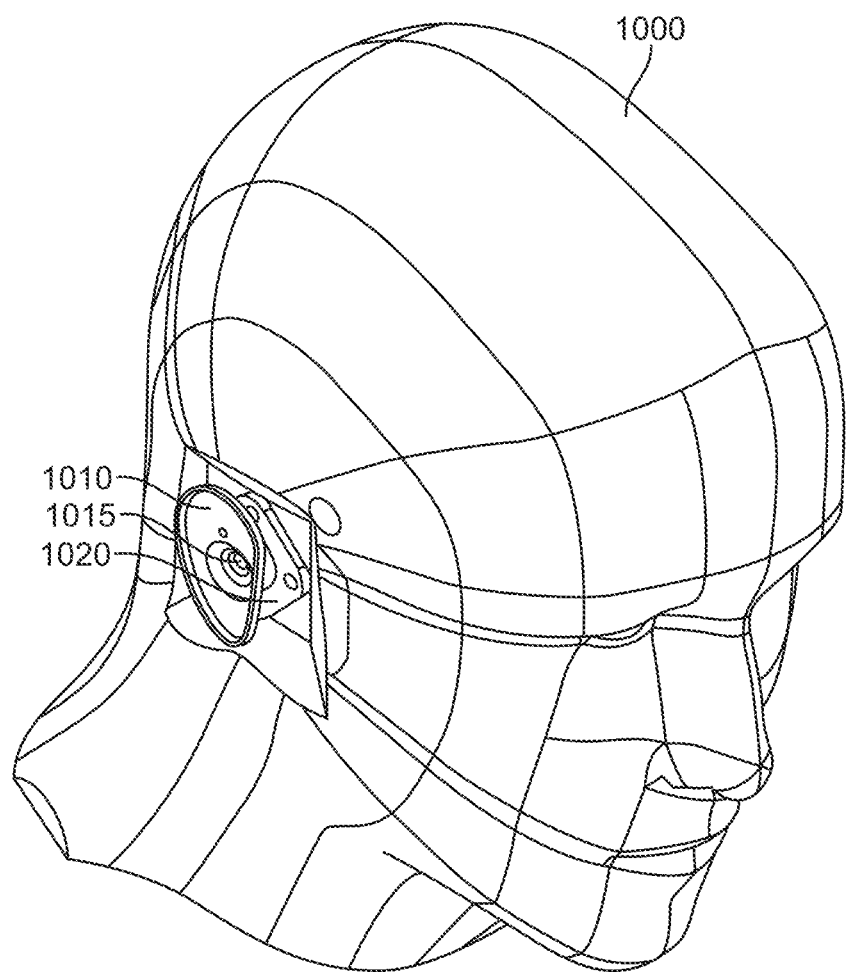
FIG. 10 illustrates an exterior isometric view of an example device for modeling properties of an ear with an artificial ear canal and pinna, in accordance with some embodiments.

FIG. 10 illustrates an exterior isometric view of an example system for modeling properties of an ear with an artificial ear canal and pinna, in accordance with some embodiments. The system may comprise a model of a head of a subject 1000. The system may comprise a mount 1020 for a device for modeling properties of an ear. The mount 1020 may be connected to a pinna 1010. The pinna may comprise an ear canal 1015. The ear canal 1015 may approximate the geometry of an ear canal of a subject. For example, the ear canal 1015 may comprise a geometry of a human adult subject or a human pediatric subject.

Figure 11A:
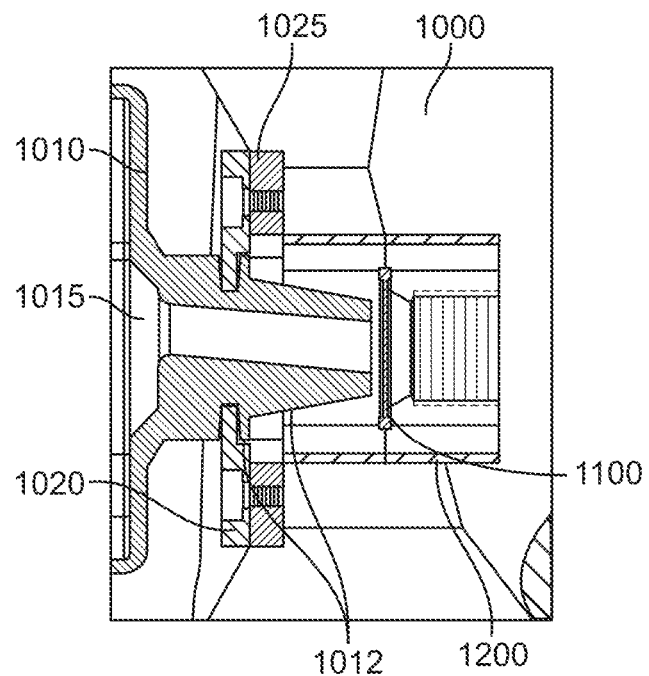
FIG. 11A illustrates a slice view of an example device for modeling properties of an ear with an artificial ear canal and pinna, in accordance with some embodiments.
Figure 11B:
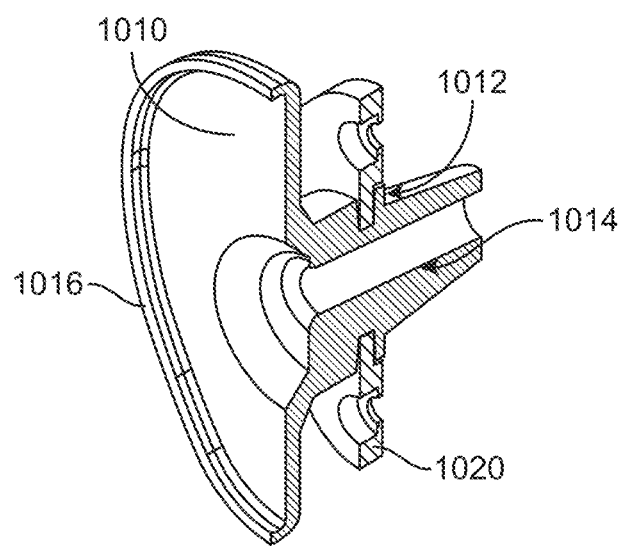
FIG. 11B illustrates an isometric slice view of an artificial ear canal and pinna of the example device of FIG. 11A, in accordance with some embodiments.

FIG. 11A illustrates a slice view of an example device for modeling properties of an ear with an artificial ear canal and pinna, in accordance with some embodiments. FIG. 11B illustrates an isometric slice view of an artificial ear canal and pinna of the example device of FIG. 11A, in accordance with some embodiments. The system may comprise a mount 1020 for a device for modeling properties of an ear. The mount 1020 may be connected to a pinna 1010. The pinna may comprise an ear canal 1015. The mount 1020 may connect to a corresponding mounting portion 1025 of a device 1200 comprising a tympanic membrane 1100. The device 1200 may comprise any embodiment, variation, or example of a device as disclosed herein. The pinna 1010 may protrude into the interior portion to form a seal 1012 with the device.

Interrogation Device

Figure 12A:
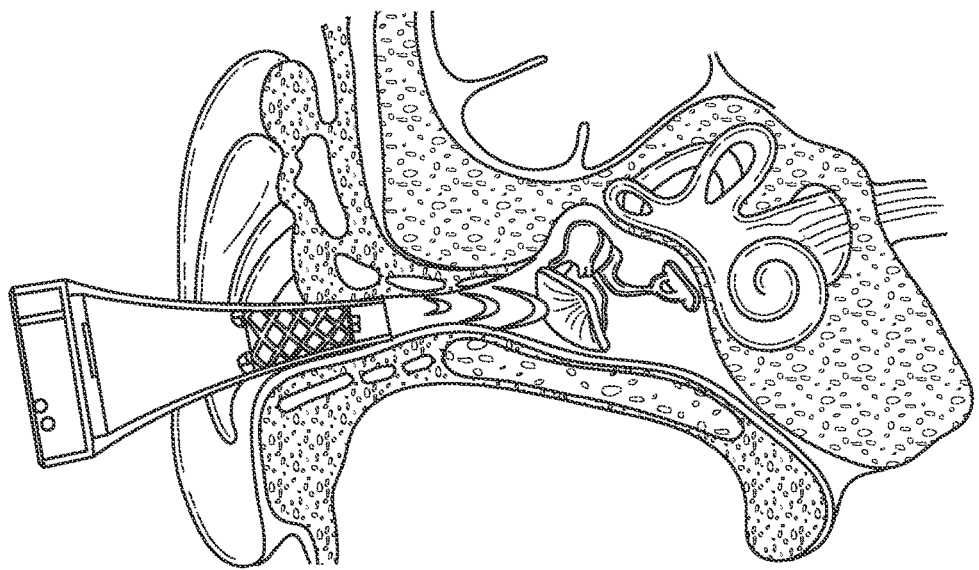
FIG. 12A illustrates a speculum of an otoscope of the present disclosure disposed within an ear of a subject.
Figure 12B:
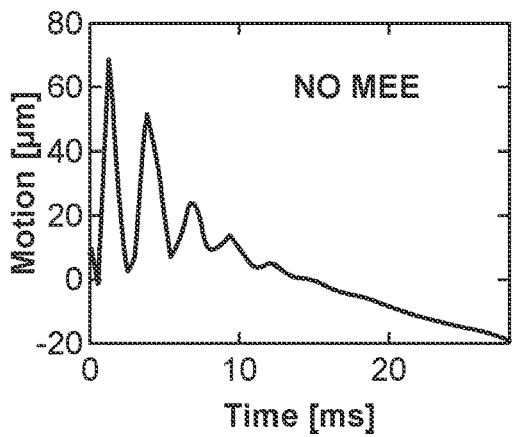
FIG. 12B, FIG. 12C, FIG. 12D, and FIG. 12E illustrate example experimental data showing how an output of an example otoscope may change with varying viscosity of an effusion behind a membrane.
Figure 12C:
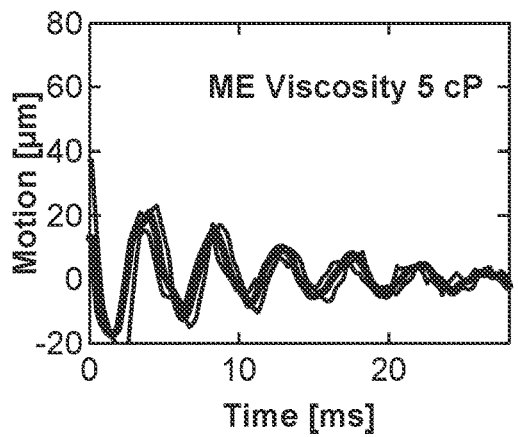
Figure 12D:
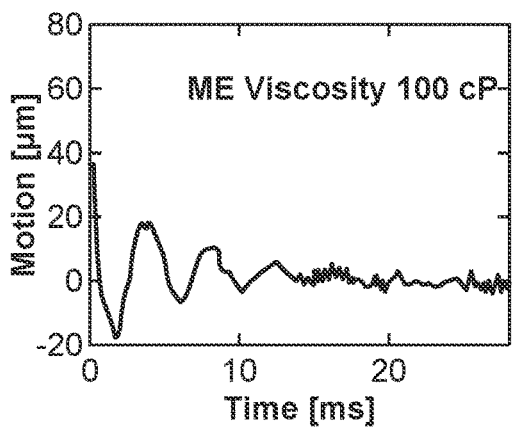
Figure 12E:
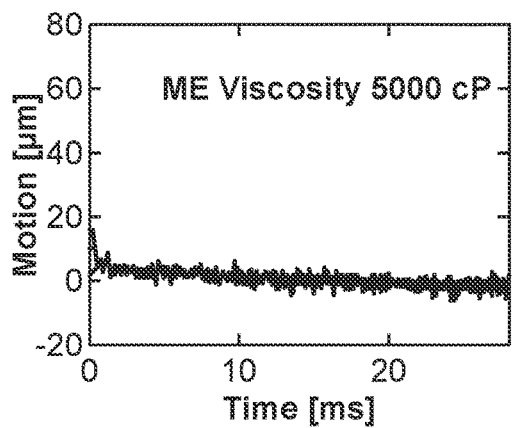

FIG. 12A illustrates a speculum of an otoscope of the present disclosure disposed within an ear of a subject. A speculum of an otoscope may be an embodiment of an interrogation device disclosed herein. The interrogation system may collect data in response to a pneumatic excitation. The interrogation system may collect data relating to a membrane movement, for example, in response to a pneumatic excitation. A pneumatic excitation may comprise a pressure excitation, such as an air puff. A pneumatic excitation may change a response of a membrane to ultrasound excitation. For example, a pneumatic excitation may cause a membrane to deflect which may change a phase of the reflected ultrasound relative to a membrane that was not exposed to the pneumatic excitation. A deflection of the membrane may comprise a damped harmonic motion. This motion may be affected by changes in the elasticity of the membrane. A change in the membrane elasticity may occur, for example, if water, bacterial growth, or other foreign material is adjacent the membrane.

In some examples, a pneumatic excitation may generate a movement of the surface or membrane during an interval of time. This interval may be coincident with acoustic wave delivered by an ultrasound transmitter to the surface or membrane. A pneumatic excitation may be continuous, may be pulsed, etc. The ultrasound reflected from the surface may be received at a transducer. A transducer may be the same transducer that generated the incident acoustic wave. A displacement of the surface or membrane may be related to a phase change in the received signal when compared to the transmit signal. A movement of the membrane may affect a phase change in the received ultrasound. A displacement may vary with time. An analysis of the temporal displacement of the surface or membrane, as measured by the phase shifts of the reflected ultrasound in response to the pneumatic excitation coupled to the surface or membrane may be used to determine the mechanical characteristics of the surface or membrane.

An analysis of the temporal information may be used in combination with the temporal displacement measured from templates of other membrane responses to create a comparison. An analysis of the temporal information may be used in combination with other metrics associated with the delay in an amplitude of reflected ultrasound, which characterizes the response of the surface or membrane. The mechanical characteristics measured may include ductility, elasticity, hardness, etc. A non-contact measurement of the mechanical properties of a surface or alternatively a fluid below the surface of a membrane may be determined.

In some embodiments, an elasticity of a surface may be measured. The phase and/or amplitude of the reflected ultrasound from the membrane may be analyzed to produce an elasticity metric. The elasticity measurement may characterize a series of measurements in response to an applied excitation. The elasticity metric may be derived from the response of the surface and may provide an indication of one or more of several different phenomena. For example, the elasticity metric may indicate whether a surface adjacent to a membrane has a gaseous boundary or fluid boundary. For example, a membrane may move less, move more slowly, and or not move at all if the membrane has a fluid boundary. In an example, the elasticity metric may indicate, for the case of characterizing a fluid behind the membrane fluid boundary, the extent, or a characteristic of the fluid. In some examples, the elasticity metric may be used to measure the characteristics of an elastic fluid with or without hysteresis of response. In a fluid with a hysteresis response, the fluid may exhibit an offset in displacement response, or "memory," such that the response behavior in one direction is similar to the response behavior in the opposite direction, but only after traveling a particular displacement distance. For a hysteresis response, it may be necessary to characterize the linear behavior of the response after a particular measured displacement associated with the hysteresis of the system. A fluid elasticity metric may be determined from the characteristic response of the surface or membrane to the surface excitation and reflected ultrasound characterization.

In some embodiments, a surface deflection may be estimated. For example, the estimate of surface deflection may be derived from a measured estimate of velocity, acceleration, or any other metric associated with deflection over time. For example, a displacement of the surface will result in a shortened path from the transducer to the surface, and the reflected signal from the surface back to the transducer will return with a phase shift. The phase shift of the reflected ultrasound relative to an excitation thus confers information about an amount of deflection. With an estimate of the force applied by the excitation, an estimate of the elasticity of the membrane can be estimated.

FIG. 12B, FIG. 12C, FIG. 12D, and FIG. 12E illustrate example experimental data showing how an output of an example otoscope may change with varying viscosity of an effusion behind a membrane. In an example, the excitation is a step or impulse response with a rising edge, falling edge, or impulsive excitation. The impulse excitation starts an oscillating deflection of the membrane. The reflected ultrasound can be measured from the time of excitation through the damping period of the oscillation of the membrane. In some embodiments, an estimate of position, elasticity, or viscosity may be performed by examination of a ringdown characteristic. For example, the ringdown characteristic may comprise at least one of an exponential decay time or a ring cycle interval or frequency, such as the decomposition of a response into a ringdown characteristic, such as:

$$\phi(t)=e^{-t/\tau}\cos(2\pi ft)$$

where:
$\phi(t)$ is the captured phase for a series of measurements;
$\tau$ is the exponential decay coefficient;
f is the ring cycle frequency; and
t is time.

The damping constant of the oscillator may relate to energy lost from the membrane into the surrounding environment. In an example, if the membrane is adjacent to a fluid, the fluid may damp the oscillation of the membrane. The viscosity of the fluid may relate to the damping of the oscillator. The ring cycle frequency may relate to the restoring constant of the elastic membrane. The restoring constant may be related to the elasticity of the membrane. The restoring constant may be related to the viscosity of a fluid adjacent the membrane. The ring cycle frequency may be higher the lower the viscosity of a fluid adjacent the membrane.

Each excitation event may start a new deflection of the membrane. For example, an impulse excitation may pull the membrane in or push the membrane out for a limited period of time. For example, a square wave excitation may pull the membrane in or push the membrane out for a longer time. For example, a sine wave or other more complex excitation may be applied and the observed ringdown at the transducer may be a cross-correlation of the excitation field with the responding field. A pneumatic excitation may be applied at a frequency of less than 100 kHz, less than 1 kHz, less than 100 Hz, less than 10 Hz, less than 1 Hz, or less, or within a range given by any two the preceding values. A pneumatic excitation may be applied at a frequency greater than 1 Hz, greater than 10 Hz, greater than 100 Hz, greater than 1 kHz, greater than 100 kHz or more, or within a range given by any two the preceding values. A pneumatic excitation may be applied within a range between 10 Hz and 100 Hz.

In an example, an interrogation system as disclosed herein may comprise an embodiment, variation, or example of the methods and systems disclosed in U.S. Pat. No. 7,771,356 and U.S. Patent Publication Nos. 2019/0365292, 2018/0310917, and 2017/0014053, which are each incorporated herein by reference in their entirety. Methods and systems for obtaining information regarding the motion of a tympanic membrane using ultrasound echo signals as disclosed in the incorporated references may be used to generate one or more parameters related to a dynamic property of the tympanic membrane. A system for measuring ultrasound echo signal may induce motion of the tympanic membrane by applying a systematic pressure pulse and then extracting Doppler shift signals from ultrasound waves to analyze displacement of the TM and/or categorize viscosity of ear effusion.

In an example, an interrogation system as disclosed herein may comprise an embodiment, variation, or example of the methods and systems disclosed in commonly assigned U.S. Patent Publication No. 2019/0200873 and U.S. Patent Publication No. 2017/0360302, each of which is incorporated herein by reference in its entirety. Methods and systems for characterizing a membrane using optical coherence tomography (OCT) as disclosed in U.S. Patent Publication No. 2019/0200873 and U.S. Patent Publication No. 2017/0360302 may be used to generate one or more parameters related to a dynamic property of the tympanic membrane. For example, a dynamic property of the tympanic membrane may comprise a phase delay or a time delay in the reflected optical signal in response to an applied pneumatic excitation. OCT may be used to collect depth dependent data related to the tympanic membrane. OCT may be used to collect frequency dependent data, such as wavelength of absorption of a membrane or a fluid adjacent a membrane.

Figure 14:
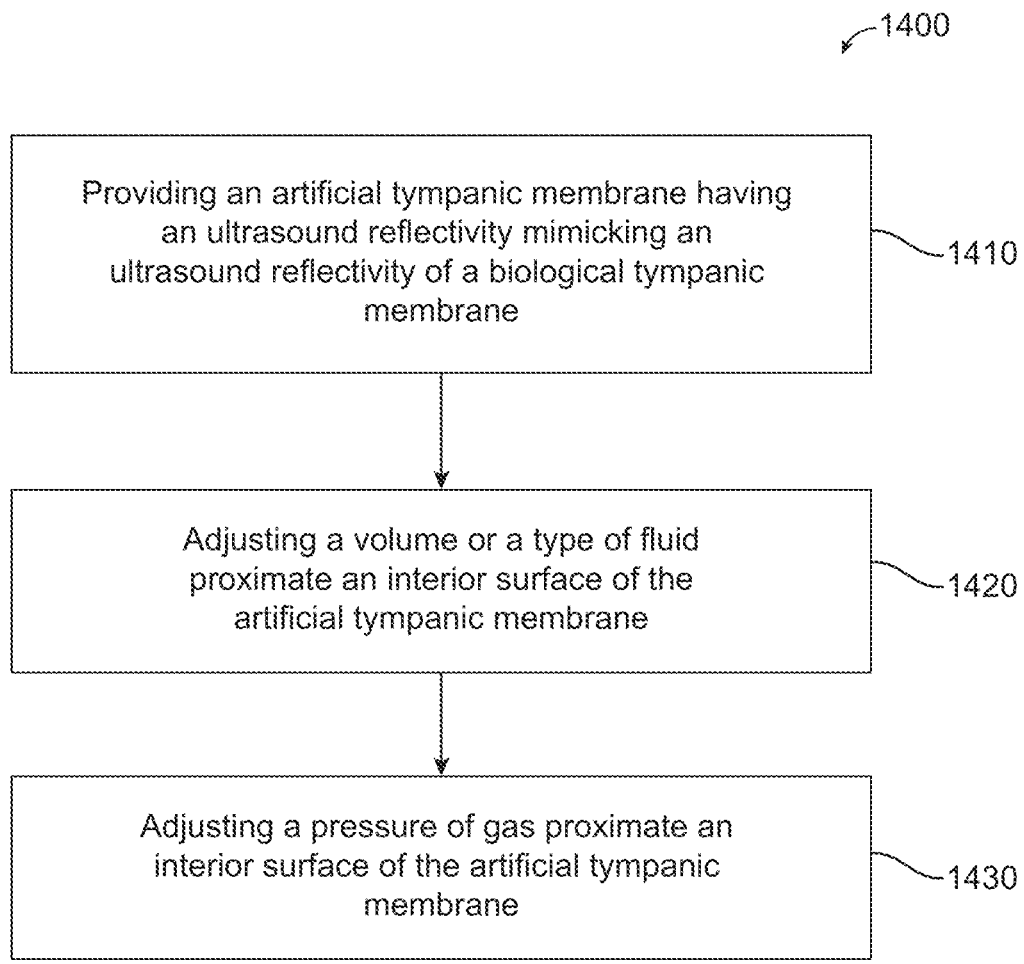
FIG. 14 is a flow chart of an example method of testing an otoscope using a model ear, in accordance with some embodiments.

FIG. 14 is a flow chart of an example method 1400 of testing an otoscope using a model ear, in accordance with some embodiments. A method 1400 may comprise providing an artificial tympanic membrane. The artificial tympanic membrane may have an ultrasound reflectivity mimicking an ultrasound reflectivity of a biological tympanic membrane, according to an operation 1410. A method 1400 may comprise adjusting a volume of or a type of fluid proximate an interior surface of the artificial tympanic membrane, according to an operation 1420. A method 1400 may comprise adjusting a pressure of gas proximate an interior surface of the artificial tympanic membrane, according to an operation 1430.

In some cases, the adjusting one or more of the volume of fluid, the type of fluid, or the pressure of gas may change a membrane deflection or a membrane movement to controllably mimic a disease state of an ear. In some cases, adjusting the type of fluid comprises varying a viscosity of fluid. In some cases, wherein the disease state of the ear is a bacterial or a viral ear infection.

In some cases, the method 1400 further comprises aligning an otoscope to locate the artificial tympanic membrane based on an optical reflection from the artificial tympanic membrane surface. In some cases, the optical reflection is exhibited on an anterior inferior quadrant of the artificial tympanic membrane. In some cases, the artificial tympanic membrane has one or more visual cues, wherein the visual cues comprise exhibiting at least partially a shape of an umbo or a malleus.

In some cases, the method 1400 further comprises adjusting a movement of the artificial tympanic membrane according to a set of ordinal values or according to a continuous scale.

In some cases, the method 1400 further comprises directing a speculum of an acoustic otoscope toward the artificial tympanic membrane, wherein the artificial tympanic membrane is at least one of distensible or retractable and is configured to move in response to an applied pneumatic pressure change. In some cases, the adjusting of one or more of the volume of fluid, the type of fluid, or the gas pressure changes a rate of the membrane movement to controllably mimic a disease state of an ear.

In some cases, the method 1400 further comprises providing an artificial ear canal having an approximate geometry of a human pediatric subject or a human adult subject. In some cases, the method 1400 further comprises adjusting a tension in a mock ossicular chain coupled to the artificial tympanic membrane. In some cases, a shape and a durometer of the artificial tympanic membrane is configured to mimic a presence of an ossicular chain.

In some cases, the method 1400 further comprises injecting a fluid proximate the interior surface using a fluid injector. In some cases, the adjusting the pressure of gas proximate the interior surface comprises opening or closing an internal air valve and activating an internal air pump. In some cases, the method 1400 further comprises measuring the pressure of gas proximate the interior surface using an internal pressure gauge. In some cases, the method 1400 further comprises measuring the pressure of gas proximate an exterior surface of the artificial tympanic membrane using an external pressure gauge. In some cases, the method 1400 further comprises adjusting the pressure of gas proximate an exterior surface of the artificial tympanic membrane using an external air pump.

In some cases, the method 1400 further comprises using a processor to control the operation of one or more of the fluid injector, the internal air valve, the internal air pump, the internal pressure gauge, the external pressure gauge, the external air pump, or a display visible to a user. In some cases, the method 1400 further comprises receiving pressure data from one or more of the internal pressure gauge or the external pressure gauge at a processor. In some cases, the method 1400 further comprises using the pressure data to adjust one or more of: the volume of fluid proximate the interior surface; the pressure of gas proximate the interior surface; and the pressure of gas proximate the exterior surface.

Although the above operations show a method 1400 for modeling an ear, in accordance with some embodiments, a person of ordinary skill in the art will recognize many variations based on the teachings described herein. The steps may be completed in any order. Steps may be added or deleted. Some of the steps may comprise sub-steps. Many of the steps may be repeated as often as beneficial to the method.

Figure 15:
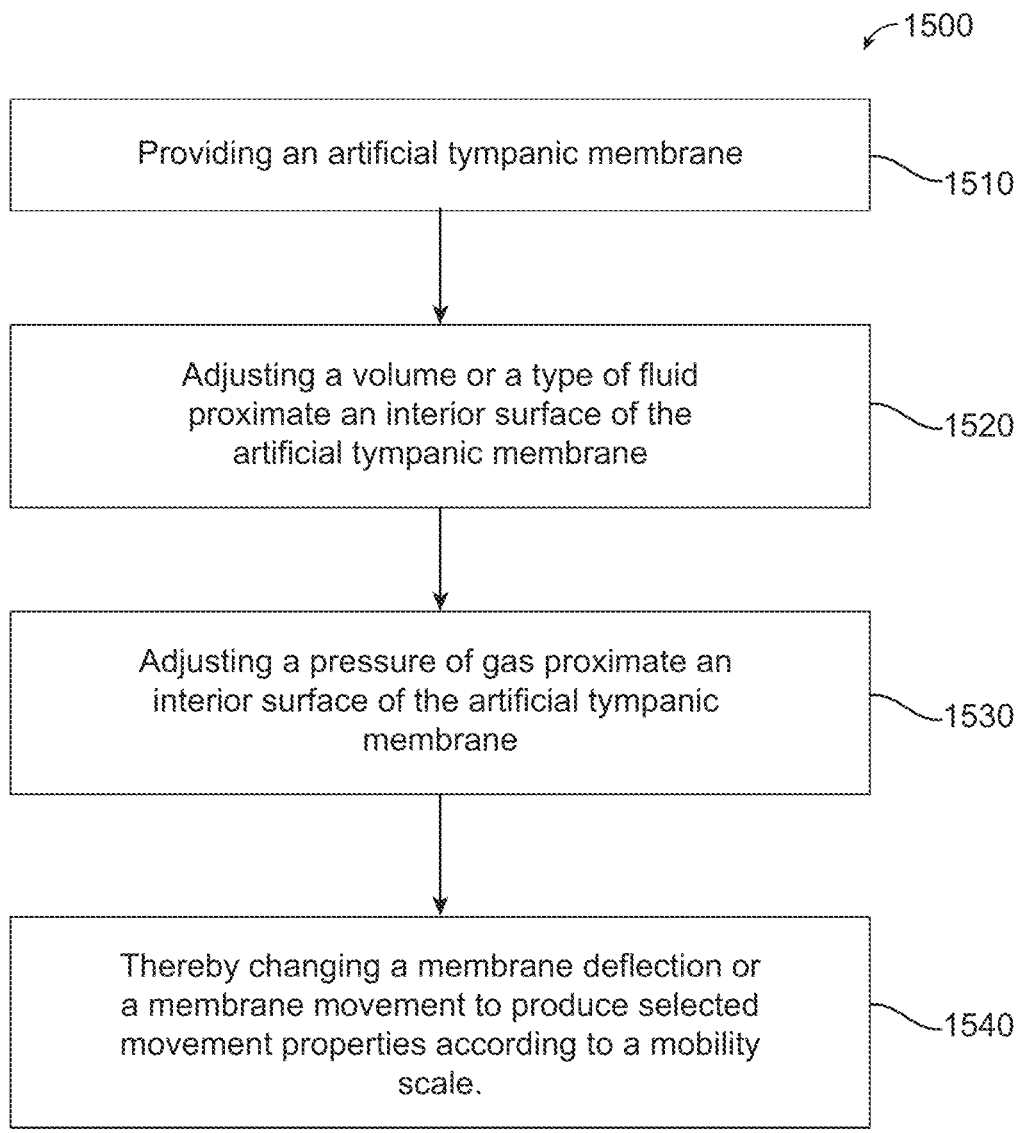
FIG. 15 is a flow chart of another example method of testing an otoscope using a model ear, in accordance with some embodiments.

FIG. 15 is a flow chart of another example method 1500 of testing an otoscope using a model ear, in accordance with some embodiments. A method 1500 may comprise providing an artificial tympanic membrane, according an operation 1510. A method 1500 may comprise adjusting a volume or a type of fluid proximate an interior surface of the artificial tympanic membrane, according an operation 1520. A method 1500 may comprise adjusting a pressure of gas proximate an interior surface of the artificial tympanic membrane, according an operation 1530. A method 1500 may adjusting of the volume or the type of fluid and adjusting of the pressure of gas by changing a membrane movement to produce selected movement properties according to a mobility scale, according an operation 1540.

In some cases, adjusting one or more of the volume of fluid, the type of fluid, or the pressure of gas changes a membrane deflection or a membrane movement to controllably mimic the disease state of the ear. In some cases, the disease state of the ear is a bacterial or a viral ear infection. In some cases, the adjustment of the type of fluid comprises varying a viscosity of fluid.

In some cases, the method 1500 further comprises aligning an otoscope to locate the artificial tympanic membrane based on an optical reflection from the artificial tympanic membrane surface. In some cases, the optical reflection is exhibited on an anterior inferior quadrant of the artificial tympanic membrane. In some cases, the artificial tympanic membrane has one or more visual cues, wherein the visual cues comprise exhibiting at least partially a shape of an umbo or a malleus.

In some cases, the mobility scale comprises a set of ordinal values or a continuous scale.

In some cases, the method 1500 further comprises directing a speculum of an acoustic otoscope toward the artificial tympanic membrane, wherein the artificial tympanic membrane is at least one of distensible or retractable and is configured to move in response to an applied pneumatic pressure change.

In some cases, adjusting of one or more of the volume of fluid, the type of fluid, or the gas pressure changes a rate of the membrane movement to controllably mimic a disease state of an ear.

In some cases, the method 1500 further comprises providing an artificial ear canal having an approximate geometry of a human pediatric subject or a human adult subject. In some cases, the interior portion comprises a mock ossicular chain coupled to the tympanic membrane. In some cases, the method 1500 further comprises adjusting a tension in a mock ossicular chain coupled to the artificial tympanic membrane. In some cases, a shape and a durometer of the artificial tympanic membrane is configured to mimic a presence of an ossicular chain.

In some cases, the method 1500 further comprises injecting a fluid proximate the interior surface using a fluid injector. In some cases, the method 1500 further comprises adjusting the pressure of gas proximate the interior surface comprises opening or closing an internal air valve and activating an internal air pump. In some cases, the method 1500 further comprises measuring the pressure of gas proximate the interior surface using an internal pressure gauge. In some cases, the method 1500 further comprises measuring the pressure of gas proximate an exterior surface of the artificial tympanic membrane using an external pressure gauge. In some cases, the method 1500 further comprises adjusting the pressure of gas proximate an exterior surface of the artificial tympanic membrane using an external air pump.

In some cases, the method 1500 further comprises using a processor to control the operation of one or more of the fluid injector, the internal air valve, the internal air pump, the internal pressure gauge, the external pressure gauge, the external air pump, or a display visible to a user. In some cases, the method 1500 further comprises receiving pressure data from one or more of the internal pressure gauge or the external pressure gauge. In some cases, the method 1500 further comprises using the pressure data to adjust one or more of: the volume of fluid proximate the interior surface; the pressure of gas proximate the interior surface; and the pressure of gas proximate the exterior surface.

Although the above operations show a method 1500 for modeling an ear, in accordance with some embodiments, a person of ordinary skill in the art will recognize many variations based on the teachings described herein. The steps may be completed in any order. Steps may be added or deleted. Some of the steps may comprise sub-steps. Many of the steps may be repeated as often as beneficial to the method.

Disclosed herein is a method of testing an otoscope using a model ear, including an artificial tympanic membrane. In some cases, the method may comprise providing an artificial tympanic membrane. In some cases, the method may comprise adjusting a volume of and/or a type of fluid proximate an interior surface of the artificial tympanic membrane. In some cases, the method may comprise adjusting a pressure of gas proximate an interior surface of the artificial tympanic membrane. In some cases, adjusting of two or more of the volume of fluid, the type of fluid, or the pressure of gas changes a membrane deflection or a membrane movement to controllably mimic a disease state of an ear.

Digital Processing Device

Figure 16:
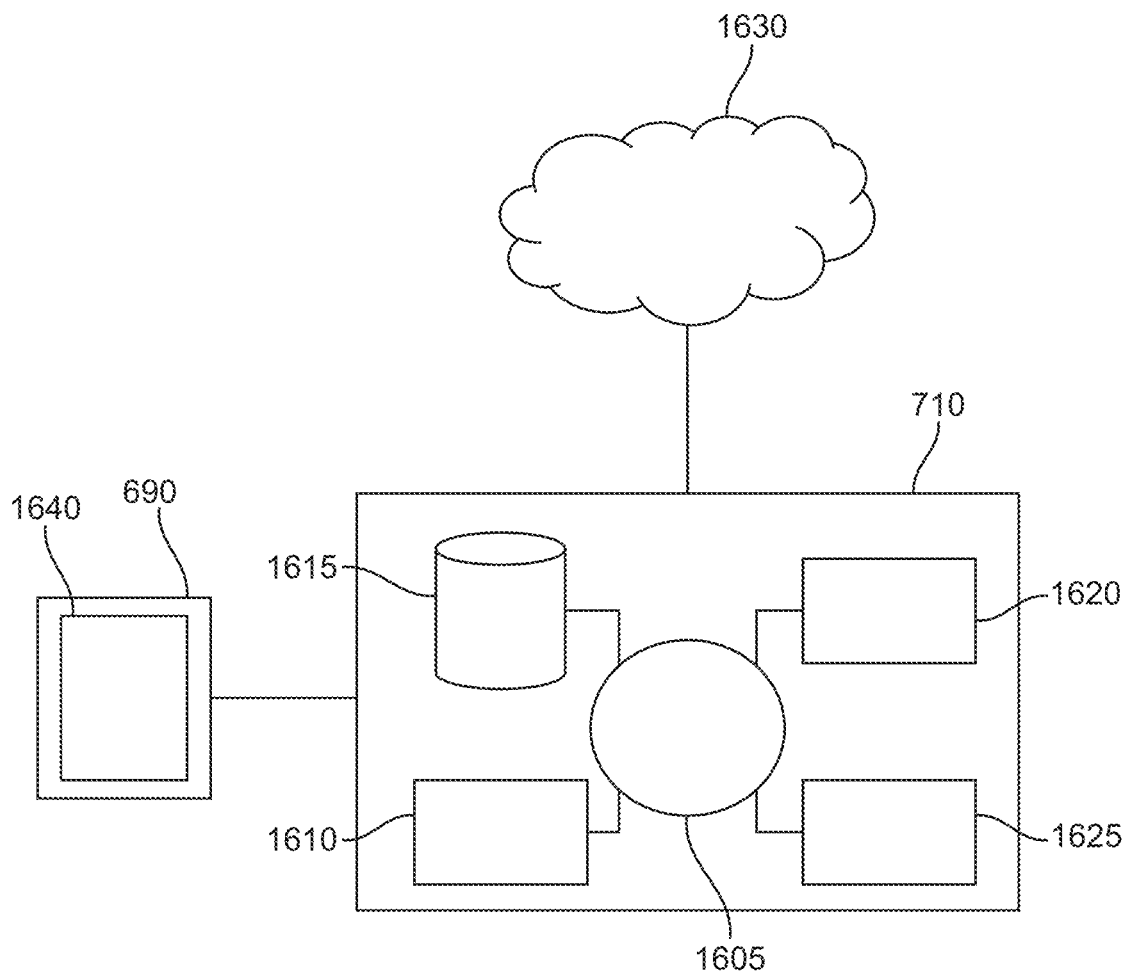
FIG. 16 is a schematic diagram illustrating of an example device for modeling properties of an ear comprising a digital processing device and a display visible to a user, in accordance with some embodiments.

FIG. 16 is a schematic diagram illustrating of an example device for modeling properties of an ear comprising a digital processing device and a display visible to a user, in accordance with some embodiments.

In some embodiments, devices, systems, and methods of use thereof described herein include a digital processing device or use of the same. For example, a digital processing device may be used to control various aspects of the devices, methods, and systems disclosed herein. For example, a digital processing device may be used to perform one or more operations of a method of testing an otoscope using a model ear, including an artificial tympanic membrane. A digital processing device may comprise a computing system, for example, the computing system comprising a memory, the memory comprising instructions for performing one or more steps of a method of testing a tympanic membrane. The digital processing device may be configured to perform one or more steps of the method 1400 or the method 1500, as disclosed herein. The digital processing device may be configured to control the operation of one or more of: the fluid injector, the internal air valve, the internal air pump, the internal pressure gauge, the external pressure gauge, the external air pump, or a display visible to a user. A digital processing device may be configured to receive pressure data from one or more of the internal pressure gauge or the external pressure gauge. A digital processing device may receive and/or retrieve one or more datasets from a device or a system as disclosed herein. The digital processing device may be configured to use the pressure data to adjust one or more of the volume of fluid proximate the interior surface; the pressure of gas proximate the interior surface; and the pressure of gas proximate the exterior surface. A digital processing device may comprise database management systems for the one or more datasets.

In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device may be optionally connected a computer network. In further embodiments, the digital processing device is optionally connected to the internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random-access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Referring to FIG. 16, in a particular embodiment, an example digital processing device 710 is programmed or otherwise configured control to or to implement the devices and methods as described herein. The device 710 may regulate various aspects of the devices and methods for modeling an ear of the present disclosure, such as, for example, performing processing steps. In this embodiment, the digital processing device 710 includes a central processing unit (CPU, also "processor" and "computer processor" herein) 1605, which may be a single core or multi core processor, or a plurality of processors for parallel processing. The digital processing device 710 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 may be a data storage unit (or data repository) for storing data. The digital processing device 710 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the device 710, can implement a peer-to-peer network, which may enable devices coupled to the device 710 to behave as a client or a server.

Continuing to refer to FIG. 16, the CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and write back. The CPU 1605 can be part of a circuit, such as an integrated circuit. One or more other components of the device 710 can be included in the circuit. In some cases, the circuit is an application specific integrated circuit (ASIC) or a field programmable gate array (FPGA).

Continuing to refer to FIG. 16, the storage unit 1615 can store files, such as drivers, libraries, and saved programs. The storage unit 1615 can store user data, e.g., user preferences and user programs. The digital processing device 710 in some cases can include one or more additional data storage units that are external, such as located on a remote server that is in communication through an intranet or the Internet. The digital processing device 710 can communicate with one or more remote computer systems through the network 1630. For instance, the device 710 can communicate with a remote computer system of a user.

Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 710, such as, for example, on the memory 1610 or electronic storage unit 1615. The machine executable or machine-readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

The digital processing device 710 can include or be in communication with an electronic display 690 that comprises a user interface (UI) 1640. Examples of UI's include, without limitation, a graphical user interface (GUI) and web-based user interface. In some cases, electronic display 690 may be connected to the computer system 710 via a network, e.g., via network 1630.

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the platforms, systems, media, and methods disclosed herein include one or more databases, or use of the same. In view of the disclosure provided herein, those of skill in the art will recognize that many databases are suitable for storage and retrieval of datasets from an interrogation system, storage classified datasets, determination of parameters from the one or more datasets, storage of parameters associated with classified datasets, etc. In various embodiments, suitable databases include, by way of non-limiting examples, relational databases, non-relational databases, object-oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

EXAMPLES

Figure 13:
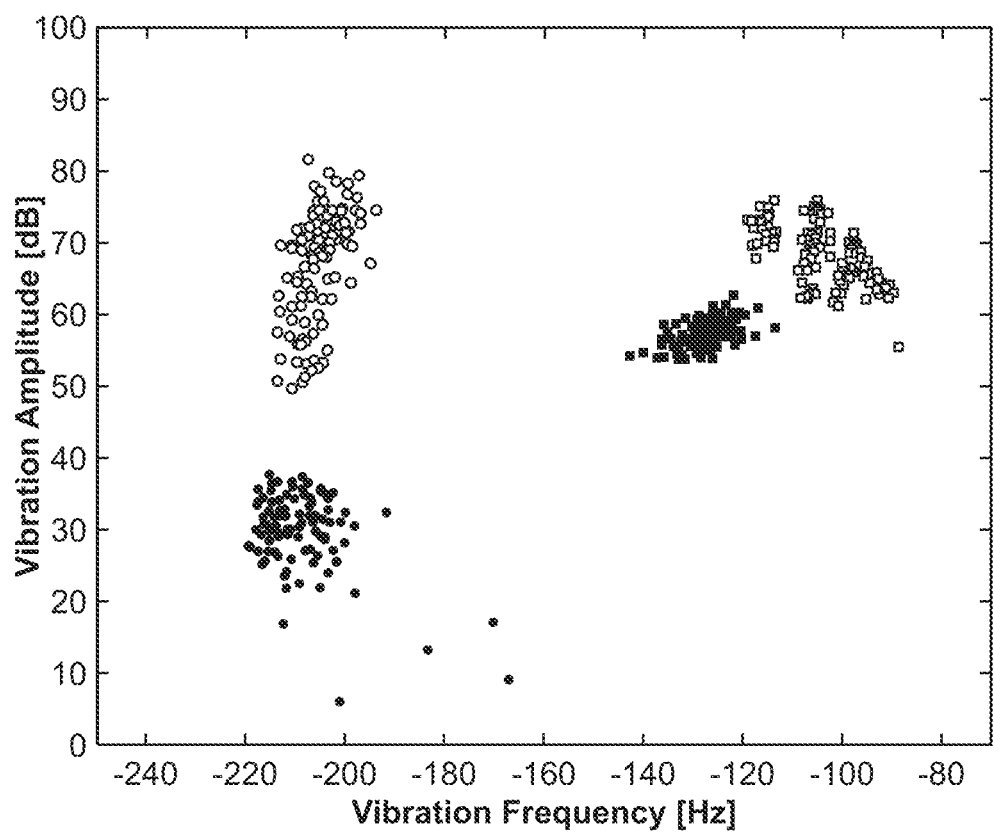
FIG. 13 illustrates example experimental data showing various classes of effusion can be identified based on vibration frequency and amplitude.

FIG. 13 illustrates example experimental data taking using Doppler ultrasound measurements made in response to a pneumatic challenge. The data show that various classes of effusion could be identified based on vibration frequency and amplitude. The data points in the upper left-hand corner were from samples with air behind the membrane (e.g., no effusion) and show high vibration frequency and high amplitude. The data points in the lower left-hand corner were from samples with highly viscous effusions and show high frequency and very low amplitude. The data points in upper right-hand corner were from samples with moderately and less viscous fluids and show high amplitude and low frequency vibrations.

The following data tables show example experimental data showing the adjustment of a device of the present disclosure to produce selected movement properties according to a mobility scale. We used different durometer artificial tympanic membranes which varied from durometer 20 A to Shore durometer 70 A. We set up clinicians to view the artificial tympanic membranes with a standard otoscope fitted with a manual insufflation bulb for pneumatic otoscopy. Our clinicians were pediatricians who regularly used pneumatic otoscopy in their practice. The ear phantom was also set up to have the external ear canal either opened (i.e. open seal) to the environment such that the insufflation system. The entrance to the external ear canal had an elastomeric covering over the entrance aperture with a 2 mm diameter hole. This allows the outer surface of the speculum to make an adequate seal with external ear canal.

The scale for tympanic membrane mobility in response to the insufflation was observation based on the clinician's expected movement of an in vivo tympanic membrane where "3" was normal, "2" slightly too mobile, "1" too mobile, "4" slightly too stiff, "5" too stiff From the data, we determined the average closest to normal was the 70 A. We also determined the open condition introduced too much uncertainty in tympanic membrane mobility and represented too much of leak state. We presented the tympanic membrane durometers in a random order to reduce pattern recognition-induced observation bias.

We repeated the same method with artificial tympanic membranes that ranged around the Shore 70 A value. For this set, we did not use the "open" position on the external ear canal seal. We found that the values which approached the average measures of normal were the Shore 70 A and 80 A artificial tympanic membranes.

TABLE 1

Test 1

| Seal Position | Clinician # | Durometer 70A | | 70A | 45A | | 45A | 20A | | 20A |
|---|---|---|---|---|---|---|---|---|---|---|
| Closed | 1 | Normal | | 3 | Too mobile | | 1 | Too mobile | | 1 |
| Closed | 2 | Normal | | 3 | Normal | | 3 | Too mobile | | 1 |
| Closed | 3 | Too mobile | | 1 | Too mobile | | 1 | Too mobile | | 1 |
| Closed | 4 | Too stiff | | 5 | normal | | 3 | normal | | 3 |
| Closed | 5 | Too stiff | | 5 | normal | | 3 | Too mobile | | 1 |
| | | | | 3.4 | | | 2.2 | | | 1.4 |
| Open | 1 | Too stiff | | 5 | Too stiff | | 5 | Too mobile | | 1 |
| Open | 2 | Slightly too stiff | | 4 | Too stiff | | 5 | Too mobile | | 1 |
| Open | 3 | Too stiff | | 5 | Too mobile | | 1 | Too mobile | | 1 |
| Open | 4 | Too stiff | | 5 | Slightly too stiff | | 4 | Slightly too stiff | | 4 |
| Open | 5 | Too stiff | | 5 | Too stiff | | 5 | too mobile | | 1 |

TABLE 2

Test 2

| Seal Position | Clinician # | Durometer 80A | | 80A | 70A | | 70A | 60A | | 60A | 50A | | 50A |
|---|---|---|---|---|---|---|---|---|---|---|---|---|---|
| Closed | 1 | Normal | | 3 | Normal | | 3 | Too mobile | | 1 | Too mobile | | 1 |
| Closed | 2 | Slightly too stiff | | 4 | Normal | | 3 | Too mobile | | 1 | Too mobile | | 1 |
| Closed | 3 | Normal | | 3 | Slightly too stiff | | 4 | Slightly too mobile | | 2 | Too mobile | | 1 |
| Closed | 4 | Slightly too stiff | | 4 | Normal | | 3 | Slightly too stiff | | 4 | Slightly too mobile | | 2 |
| Closed | 5 | Slightly too stiff | | 4 | Too stiff | | 5 | Slightly too mobile | | 2 | Too mobile | | 1 |
| | | | | 3.6 | | | 3.6 | | | 2 | | | 1.2 | action would be slightly diminished due to a leak or with the external ear canal closed ("closed seal") to the environment. A needle valve was used to adjust the dampening of the While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for modeling properties of an ear, including a tympanic membrane, the device comprising: an artificial tympanic membrane having an ultrasound reflectivity mimicking an ultrasound reflectivity of a biological tympanic membrane; a housing coupled to the artificial tympanic membrane and further defining an interior portion coupled to an interior surface of the artificial tympanic membrane, the interior portion having an adjustable volume of fluid or an adjustable type of fluid, and the interior portion having an adjustable gas pressure; and a processor configured to control the operation of one or more of: a fluid injector, an internal air valve, an internal air pump, an internal pressure gauge, an external pressure gauge, or an external air pump.

2. The device of claim 1, wherein adjustment of one or more of the volume of fluid, the type of fluid, or the gas pressure changes a membrane deflection or a membrane movement to controllably mimic a disease state of the ear.

3. The device of claim 1, wherein adjustment of the type of fluid changes a membrane deflection or a membrane movement to controllably mimic a disease state of the ear, and the adjustment of the type of fluid comprises varying a viscosity of fluid.

4. The device of claim 2, wherein the disease state of the ear is a bacterial or a viral ear infection.

5. The device of claim 1, wherein the artificial tympanic membrane has a shape which exhibits an optical reflection from the artificial tympanic membrane surface to enable location of the artificial tympanic membrane and alignment of an otoscope.

6. The device of claim 1, wherein the artificial tympanic membrane has one or more visual cues, wherein the visual cues comprise exhibiting at least partially a shape of an umbo or a malleus.

7. The device of claim 1, wherein the artificial tympanic membrane is one or more of distensible or retractable and is further configured to move in response to an applied pneumatic pressure change.

8. The device of claim 1, wherein adjustment of one or more of the volume of fluid, the type of fluid, or the gas pressure changes a rate of a membrane movement to controllably mimic a disease state of the ear.

9. The device of claim 1, wherein the housing further defines an exterior portion, wherein the exterior portion comprises an artificial ear canal having an approximate geometry of a human pediatric subject or a human adult subject.

10. The device of claim 1, wherein the interior portion comprises a mock ossicular chain coupled to the artificial tympanic membrane.

11. The device of claim 10, wherein the mock ossicular chain has a controllable tension.

12. The device of claim 1, wherein a shape and a hardness of the artificial tympanic membrane is configured to mimic a presence of an ossicular chain.

13. The device of claim 1, wherein the interior portion comprises an opening for a fluid injector or the fluid injector.

14. The device of claim 1, wherein the interior portion comprises an internal air valve and an internal air pump or an opening for an internal air valve and an internal air pump.

15. The device of claim 1, wherein the housing further defines an exterior portion coupled to an exterior surface of the artificial tympanic membrane.

16. The device of claim 1, wherein the processor is configured to receive pressure data from one or more of the internal pressure gauge or the external pressure gauge.

17. The device of claim 16, wherein the pressure data is used to adjust one or more of: the adjustable volume of fluid proximate the interior surface; the adjustable gas pressure proximate the interior surface; or a gas pressure proximate the exterior surface.

18. A method of testing an otoscope using a model ear, including an artificial tympanic membrane, the method comprising: providing the artificial tympanic membrane having an ultrasound reflectivity mimicking an ultrasound reflectivity of a biological tympanic membrane; adjusting a volume of or a type of fluid proximate an interior surface of the artificial tympanic membrane; adjusting a pressure of gas proximate the interior surface of the artificial tympanic membrane; and at a processor, operably coupled to the artificial tympanic membrane: controlling the operation of one or more of: a fluid injector, an internal air valve, an internal air pump, an internal pressure gauge, an external pressure gauge, or an external air pump.

19. A device for modeling properties of an ear, including a tympanic membrane, the device comprising: an artificial tympanic membrane; a housing coupled to the artificial tympanic membrane and further defining an interior portion coupled to an interior surface of the artificial tympanic membrane, the interior portion having an adjustable volume or an adjustable type of fluid and an adjustable gas pressure; wherein adjustment of the volume or type of fluid and the gas pressure changes a membrane movement to produce selected movement properties according to a mobility scale; and a processor configured to control the operation of one or more of: a fluid injector, an internal air valve, an internal air pump, an internal pressure gauge, an external pressure gauge, or an external air pump.

* * * * *